(12) United States Patent
Azamian et al.

(10) Patent No.: US 12,171,750 B2
(45) Date of Patent: *Dec. 24, 2024

(54) ISOXAZOLINE PARASITICIDE FORMULATIONS AND METHODS FOR TREATING BLEPHARITIS

(71) Applicant: Tarsus Pharmaceuticals, Inc., Irvine, CA (US)

(72) Inventors: Bobak Robert Azamian, Newport Coast, CA (US); Douglas Michael Ackermann, Reno, NV (US); Shawn D. Hickok, Aliso Viejo, CA (US); Joseph G. Vehige, Irvine, CA (US)

(73) Assignee: Tarsus Pharmaceuticals, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/325,919

(22) Filed: May 30, 2023

(65) Prior Publication Data

US 2023/0293496 A1 Sep. 21, 2023

Related U.S. Application Data

(63) Continuation of application No. 17/099,531, filed on Nov. 16, 2020, which is a continuation of application No. 16/221,390, filed on Dec. 14, 2018, now Pat. No. 10,835,517.

(60) Provisional application No. 62/746,498, filed on Oct. 16, 2018, provisional application No. 62/689,787, filed on Jun. 25, 2018, provisional application No. 62/626,612, filed on Feb. 5, 2018, provisional application No. 62/615,855, filed on Jan. 10, 2018, provisional application No. 62/599,213, filed on Dec. 15, 2017.

(51) Int. Cl.
| | | |
|---|---|---|
| *A61K 31/422* | (2006.01) | |
| *A61K 9/00* | (2006.01) | |
| *A61K 9/08* | (2006.01) | |
| *A61K 47/26* | (2006.01) | |
| *A61P 27/02* | (2006.01) | |
| *A61P 33/14* | (2006.01) | |

(52) U.S. Cl.
CPC .......... *A61K 31/422* (2013.01); *A61K 9/0048* (2013.01); *A61K 9/08* (2013.01); *A61K 47/26* (2013.01); *A61P 27/02* (2018.01); *A61P 33/14* (2018.01)

(58) Field of Classification Search
CPC .... A61K 31/422; A61K 9/0048; A61K 31/42; A61K 47/26; A61K 9/08; A61P 27/02; A61P 33/14
See application file for complete search history.

(56) References Cited

U.S. PATENT DOCUMENTS

| | | |
|---|---|---|
| 3,781,355 A | 12/1973 | Harrison et al. |
| 3,864,497 A | 2/1975 | Harrison et al. |
| 4,389,397 A | 6/1983 | Lo et al. |
| 4,957,918 A | 9/1990 | Martin et al. |
| 5,019,392 A | 5/1991 | Wallach |
| 5,338,533 A | 8/1994 | Derrieu |
| 5,614,545 A | 3/1997 | Martin et al. |
| 5,632,999 A | 5/1997 | Miller |
| 5,747,057 A | 5/1998 | Miller |
| 5,776,481 A | 7/1998 | Karst et al. |
| 5,952,372 A | 9/1999 | McDaniel |
| 5,968,990 A | 10/1999 | Jon et al. |
| 5,981,500 A | 11/1999 | Bishop et al. |
| 6,001,822 A | 12/1999 | Wicks et al. |
| 6,063,394 A | 5/2000 | Grosse-Bley et al. |
| 6,255,350 B1 | 7/2001 | Jon et al. |
| 6,500,446 B1 | 12/2002 | Derrieu et al. |
| 6,797,701 B2 | 9/2004 | Lukas et al. |
| 6,881,726 B2 | 4/2005 | Chang et al. |
| 7,064,108 B2 | 6/2006 | Guzzo et al. |
| 7,348,317 B2 | 3/2008 | Chang et al. |
| 7,531,186 B2 | 5/2009 | Boeckh et al. |
| 7,662,972 B2 | 2/2010 | Mita et al. |
| 7,906,128 B2 | 3/2011 | Heaney et al. |

(Continued)

FOREIGN PATENT DOCUMENTS

| | | |
|---|---|---|
| CN | 102260252 | 11/2011 |
| CN | 102552114 A | 7/2012 |

(Continued)

OTHER PUBLICATIONS

Abd et al., "Minoxidil Skin Delivery from Nanoemulsion Formulations Containing Eucalyptol or Oleic Acid: Enhanced Diffusivity and Follicular Targeting", Pharmaceutics 2018; 10(19) in 12 pages.
Abelson et al., "Demystifying Demulcents: A look at the varieties of this common agent and how they can help soothe patients' eyes." Review of Ophthalmology 2006: pp. 1-7.
Abelson et al., "Staying Local with Blepharitis Treatment", Review of Ophthalmology, Oct. 2012, pp. 60-62.
Aldrich et al., "Ophthalmic Preparations", Stimuli to the Revision Process, 2013, 39(5): in 21 pages.
Ali et al., "Therapeutic efficacy of poly (lactic-co-glycolic acid} nanoparticles encapsulated ivermectin (nano-ivermectin} against brugian filariasis in experimental rodent model." Parasitol Res. Feb. 2014;113(2):681-691: Abstract in 2 pages.

(Continued)

*Primary Examiner* — Kara R McMillian
(74) *Attorney, Agent, or Firm* — Knobbe, Martens, Olson & Bear, LLP

(57) ABSTRACT

Disclosed herein are methods for treating or preventing ophthalmic and dermatologic conditions in a patient, including ocular surface conditions such as blepharitis. The methods can include topically administering directly to an ocular surface of one or more eyes of a patient in need of treatment thereof an effective amount of an isoxazoline parasiticide, formamidine parasiticide, or other active ingredient, formulated into an ophthalmic composition, the ophthalmic composition further comprising a pharmaceutically acceptable vehicle. Compositions are also disclosed.

16 Claims, 5 Drawing Sheets

(56) References Cited

U.S. PATENT DOCUMENTS

| | | |
|---|---|---|
| 7,906,130 B2 | 3/2011 | Sabnis et al. |
| 7,964,204 B2 | 6/2011 | Lahm et al. |
| 8,022,089 B2 | 9/2011 | Mita et al. |
| 8,128,968 B2 | 3/2012 | Gao et al. |
| 8,138,213 B2 | 3/2012 | Mita et al. |
| 8,207,206 B2 | 6/2012 | Nicoletti et al. |
| 8,231,888 B2 | 7/2012 | Lahm et al. |
| 8,242,161 B2 | 8/2012 | Boeckh et al. |
| 8,361,974 B2 | 1/2013 | Kaoukhov et al. |
| 8,362,069 B2 | 1/2013 | Diaz-Astruc et al. |
| 8,383,659 B2 | 2/2013 | Nanchen et al. |
| 8,389,738 B2 | 3/2013 | Kousaka et al. |
| 8,450,357 B2 | 5/2013 | Soll et al. |
| 8,455,015 B2 | 6/2013 | Gao et al. |
| 8,466,115 B2 | 6/2013 | Curtis et al. |
| 8,492,311 B2 | 7/2013 | Mita et al. |
| 8,501,799 B2 | 8/2013 | Derrieu |
| 8,541,413 B2 | 9/2013 | Wong et al. |
| 8,552,218 B2 | 10/2013 | Lahm et al. |
| 8,653,116 B2 | 2/2014 | Nanchen et al. |
| 8,790,674 B2 | 7/2014 | Derrieu et al. |
| 8,796,464 B2 | 8/2014 | Moriyama et al. |
| 8,815,816 B2 | 8/2014 | Manetta et al. |
| 8,871,941 B2 | 10/2014 | Lahm et al. |
| 8,921,408 B2 | 12/2014 | Soll et al. |
| 8,946,492 B2 | 2/2015 | Mita et al. |
| 8,987,218 B2 | 3/2015 | Kaoukhov et al. |
| 9,044,389 B2 | 6/2015 | Nanchen et al. |
| 9,066,515 B2 | 6/2015 | Boeckh et al. |
| 9,089,587 B2 | 7/2015 | Jacovella et al. |
| 9,095,566 B1 | 8/2015 | Yavitz et al. |
| 9,107,812 B2 | 8/2015 | Derrieu |
| 9,131,689 B2 | 9/2015 | Derrieu et al. |
| 9,173,728 B2 | 11/2015 | Wurtz |
| 9,173,870 B2 | 11/2015 | Fuchs et al. |
| 9,186,345 B2 | 11/2015 | Snorrason |
| 9,200,003 B2 | 12/2015 | Billen et al. |
| 9,233,117 B2 | 1/2016 | Jacovella et al. |
| 9,233,118 B2 | 1/2016 | Jacovella et al. |
| 9,260,231 B2 | 2/2016 | Havrileck et al. |
| 9,457,038 B2 | 10/2016 | Kaoukhov et al. |
| 9,532,978 B2 | 1/2017 | Fuchs et al. |
| 9,730,919 B2 | 8/2017 | Snorrason |
| 9,758,491 B2 | 9/2017 | Crouse et al. |
| 9,788,994 B2 | 10/2017 | Nichamin |
| 10,588,915 B2 | 3/2020 | Alster et al. |
| 10,688,122 B2 | 6/2020 | Amselem et al. |
| 10,835,517 B2 | 11/2020 | Borak |
| 11,197,847 B2 | 12/2021 | Azamian et al. |
| 11,690,826 B2 * | 7/2023 | Azamian ............... A61P 27/02 514/378 |
| 11,690,827 B2 * | 7/2023 | Azamian ............... A61P 27/02 514/378 |
| 2003/0059382 A1 | 3/2003 | Brandt |
| 2003/0181354 A1 | 9/2003 | Abdulrazik |
| 2004/0167084 A1 | 8/2004 | Parks |
| 2006/0154901 A1 | 7/2006 | Pflugfelder et al. |
| 2008/0039519 A1 | 2/2008 | Heine |
| 2008/0089958 A1 | 4/2008 | Diehl et al. |
| 2009/0093421 A1 | 4/2009 | Kaoukhov et al. |
| 2009/0317503 A1 | 12/2009 | Adkins, Jr. et al. |
| 2010/0266628 A1 | 10/2010 | Razzak et al. |
| 2010/0273870 A1 | 10/2010 | Gao et al. |
| 2011/0033395 A1 | 2/2011 | Kaoukhov et al. |
| 2011/0059925 A1 | 3/2011 | Donnenfeld |
| 2011/0217249 A1 | 9/2011 | Dreher |
| 2011/0274631 A1 | 11/2011 | Kaoukhov et al. |
| 2012/0053140 A1 | 3/2012 | Kaoukhov et al. |
| 2013/0023490 A1 | 1/2013 | Boeckh et al. |
| 2013/0053374 A1 | 2/2013 | Inoue et al. |
| 2013/0101655 A1 | 4/2013 | Storm et al. |
| 2013/0324538 A1 | 12/2013 | Gauvry et al. |
| 2013/0344128 A1 | 12/2013 | Gao et al. |
| 2015/0086596 A1 | 3/2015 | Spallitta |
| 2016/0243116 A1 | 8/2016 | Jain |
| 2016/0256442 A1 | 9/2016 | Cady et al. |
| 2016/0287566 A1 | 10/2016 | Busby |
| 2016/0317439 A1 | 11/2016 | Lehay et al. |
| 2017/0020849 A1 | 1/2017 | Soll et al. |
| 2017/0024748 A1 | 1/2017 | Haider |
| 2017/0065565 A1 | 3/2017 | Mita et al. |
| 2017/0135978 A1 | 5/2017 | Spallitta |
| 2017/0196928 A1 | 7/2017 | McAnnally et al. |
| 2017/0232024 A1 | 8/2017 | Tan et al. |
| 2017/0239218 A1 | 8/2017 | Le Hir De Fallois et al. |
| 2017/0311601 A1 | 11/2017 | Yang et al. |
| 2020/0031859 A1 | 1/2020 | Santos et al. |
| 2020/0338105 A1 | 10/2020 | Tan et al. |
| 2021/0077465 A1 | 3/2021 | Azamian et al. |
| 2021/0077466 A1 | 3/2021 | Azamian et al. |
| 2021/0220360 A1 | 7/2021 | Kolhe |
| 2022/0160682 A1 | 5/2022 | Azamian et al. |
| 2022/0249445 A1 | 8/2022 | Azamian et al. |
| 2022/0354829 A1 | 11/2022 | Azamian et al. |
| 2022/0354830 A1 | 11/2022 | Azamian et al. |
| 2022/0362218 A1 | 11/2022 | Azamian et al. |
| 2023/0190711 A1 | 6/2023 | Azamian et al. |
| 2023/0218584 A1 | 7/2023 | Azamian et al. |
| 2023/0301971 A1 | 9/2023 | Azamian et al. |

FOREIGN PATENT DOCUMENTS

| | | |
|---|---|---|
| EP | 2 379 537 | 10/2012 |
| RU | 2126668 C1 | 7/2012 |
| RU | 2472505 | 1/2013 |
| RU | 2017100031 | 8/2018 |
| WO | WO 94/015597 | 7/1994 |
| WO | WO 99/058131 | 11/1999 |
| WO | WO 04/093886 | 11/2004 |
| WO | WO 06/050837 | 5/2006 |
| WO | WO 09/024541 | 2/2009 |
| WO | WO 13/039948 | 3/2013 |
| WO | WO 16/022066 | 2/2016 |
| WO | WO 16/102437 | 6/2016 |
| WO | WO 16/207234 | 12/2016 |
| WO | WO 17/147352 | 8/2017 |
| WO | WO 17/178416 | 10/2017 |
| WO | WO 18/081733 | 5/2018 |
| WO | WO 19/126541 | 6/2019 |
| WO | WO 21/013825 | 1/2021 |
| WO | WO 21/041773 | 3/2021 |

OTHER PUBLICATIONS

Allen, 2016, Ophthalmic preparations, Part 1: Ophthalmic solutions, International Journal of Pharmaceutical Compounding, 20:399-404.

Allergan, Inc. "Restasis® (cyclosporine ophthalmic emulsion)", Product Description; Dec. 2009 l n 7 pages.

Almasieh et al., "Structural and functional neuroprotection in glaucoma: role of galantamine-mediated activation of muscarinic acetylcholine receptors", Cell Death and Disease (2010) 1, e27; doi:10.1038/cddis.2009.23: pp. 1-11.

Alphabetic List of all veterinary anti-helminthics—Parasiteopedia Jul. 2017, in 2 pages.

American Academy of Ophthalmology [AAO] Cornea/External Disease Panel. Preferred Practice Pattern® Guidelines. Blepharitis. San Francisco, CA: American Academy of Ophthalmology; 2013. Available at: www.aao.org/ppp in 31 pages.

American Academy of Ophthalmology [AAO] Cornea/External Disease Panel. Preferred Practice Pattern® Guidelines. Blepharitis. San Francisco, CA: American Academy of Ophthalmology; 2018. Available at: www.aao.org/ppp in 38 pages.

Ames et al., "Cyclosporine ophthalmic emulsions for the treatment of dry eye: a review of the clinical evidence", Clin Investig (Lond). 2015, 5(3):267-285.

Anadón et al., "Use and abuse of pyrethrins and synthetic pyrethroids in veterinary medicine", The Vet J. 2009, 182:7-20.

Animalytix LLC. "Bimectin®—Injection for Cattle & Swine", Bimedia Inc., 2016: in 5 pages.

(56) References Cited

OTHER PUBLICATIONS

Anonymous (2014). "Safety Assessment of Tocopherols and Tocotrienols as Used in Cosmetics,"Cosmetics Ingredient Review, Washington, DC, 36 total pages.

Anonymous (1984). "Final Report on the Safety Assessment of Fossil and Synthetic Waxes,"International Journal of Toxicology 3:43-99.

Anonymous (1992). "Final Report on the Safety Assessment of Methylisothiazolinone and Methylchloroisothiazlinone," Journal of the American College of Toxicology 11 :75-128.

Anonymous (2002). "Final Report on the Safety Assessment of EDTA, calcium disodium EDTA, diammonium EDTA, dipotassium EDTA, disodium EDTA, TEA-EDTA, tetrasodium EDTA, tripotassium EDTA, trisodium EDTA, HEDTA, and trisodium HEDTA," International Journal of Toxicology 21 (Suppl. 2):95-142.

Anonymous (2013). "Amended Safety Assessment of Alkyl Esters as Used in Cosmetics," Cosmetics Ingredient Review, Washington, DC, 82 total pages.

Armstrong Rob., "The conclusion of a comparative efficacy study of fluralaner and sarolaner against the tick *Amblyomma americanum* on dogs is based on results obtained at study times that are outside the fluralaner label recommendations", Parasit Vectors. 2017, 10:159 in 2 pages.

Arrúa et al., "Comparative study of the efficacy of different treatment options in patients with chronic blepharitis", Arch Soc Esp Oftalmol. 2015, 90(3):112-118.

Asahi et al., "Differential mechanisms of action of the novel γ-aminobutyric acid receptor antagonist ectoparasiticides fluralaner (A1443) and fipronil", Pest Manag Sci. 2015, 71:91-95; Epub Mar. 31, 2014.

Asahi et al., Feb. 5, 2018, Fluxametamide: A novel isoxazoline insecticide that acts via distinctive antagonism of insect ligand-gated chloride channels, Pesticide Biochemistry and Physiology (2018), https://dot.org/10.1016/j.pestbp.2018.02.2002; Elsevier Inc.

Asbell et al., "The International Workshop on Meibomian Gland Dysfunction: Report of the Clinical Trials Subcommittee", IOVS, Special Issue 2011, 52(4):2065-2085.

Asoklis et al., "Ocular Rosacea", N Engl J Med. 2016, 374(8):771.

Australian Pesticides & Veterinary Medicines Authority; "Pastoral Ag Fluazuron pour-on tick development inhibitor for cattle", Application Summary for Application No. 104014, 2015, in 5 pages.

Australian Pesticides and Veterinary Medicines Authority [APVMA], "Safety of Fipronil in Dogs and Cats: A review of literature", 2011, pp. 1-21.

Avdeef Alex, "Solubility Temperature Dependence Predicted from 2D Structure", ADMET & DMPK 2015, 3(4):298-344.

Ayres et al., "Acne Rosacea Response to Local Treatment for Demodex Folliculorium", JAMA. 1933, 100(9):645-647.

Bahmani et al., "Comparison of effect of nicotine and levamisole and ivermectin on mortality of leech", Asian Pac J Trop Dis. 2014, 4(Suppl 1):S477-S480.

Baranowski et al., "Ophthalmic Drug Dosage Forms: Characterization and Research Methods", ScientificWorldJournal, 2014, Article ID 861904 in 15 pages.

Barnhorst et al., "The Efficacy of Topical Metronidazole in the Treatment of Ocular Rosacea", Ophthalmology 1996; 103:1880-1883.

Becskei et al., "Comparative speed of kill of oral treatments with Simparica™ (sarolaner) and Bravecto® (fluralaner) against induced infestations of hipicephalus sanguineus on dogs", Parasit Vectors. 2016: pp. 1-6.

Bernigaud et al. "Efficacy and Pharmacokinetics Evaluation of a Single Oral Dose of Afoxolaner against Sarcoptes scabiei in the Porcine Scabies Model for Human Infestation", Antimicrob Agents Chemother. 2018, 62(9):e02334-17 in 12 pages.

Beugnet et al., "Comparative efficacy of two oral treatments for dogs containing either afoxolaner or fluralaner against Rhipicephalus sanguineus sensu lato and Dermacentor reticulatus" Veterinary Parasitology 209 (2015): pp. 142-145.

Beugnet et al., "Comparative speed of efficacy against Ctenocephalides felis oftwo oral treatments for dogs containing either afoxolaner orfluralaner", Vet Parasitol. 2015, 207: pp. 297-301.

Beugnet et al., "Insecticide and acaricide molecules and/or combinations to prevent pet infestation by ectoparasites", Trends Parasitol. 2012, 28(7):267-279.

Bezerra Da Silva et al., "Effect of Donepezil, Tacrine, Galantamine and Rivastigmine on Acetylcholinesterase Inhibition in Dugesia tigrina" Molecules 2016, 21, 53:1-11.

Biernat et al., "Occurrence of Demodex species in patients with blepharitis and in healthy individuals: a 10-year observational study", Japanese Ophthalmological Society, Sep. 2018, 62:628-633.

Bimeda, "Bimectin Pour-On (Ivermectin Pour-On)", Safety Data Sheet, 2015, 77(58): in 8 pages.

Bos et al., "The 500 Dalton rule for the skin penetration of chemical compounds and drugs", Exp Dermatol. 2000, 9:165-169.

Brayden et al., "Drug Delivery Systems in Domestic Animal Species", in Handbook of Experimental Pharmacology by F. Cunningham et al. (eds.), 2010; (199):79-112.

Brimecombe et al., "Electrochemical investigation of the effect of pH and solvent on amitraz stability." J Agric Food Chem. Oct. 18, 2006, 54(21):8139-8143; Abstract in 2 pages.

Bron Anthony, "Ocular rosacea", UpToDate 2016 (www.uptodate.com), Wolters Kluwer in 24 pages.

Brown, M. et al. (2014). "Severe demodexfolliculorum-associated oculocutaneous rosacea in a girl successfully treated with ivermectin," JAMA Dermatol. 150:61-63.

Burgio et al., "A comparative laboratory trial evaluating the immediate efficacy of fluralaner, afoxolaner, sarolaner and imidacloprid + permethrin against adult *Rhipicephalus sanguineus* (sensu lato) ticks attached to dogs", Parasit Vectors. 2016, 9:626 in 6 pages.

Campbell William C., "Ivermectin as an Antiparasitic Agent for Use in Humans", Annu Rev Microbial. 1991, 45:445-474.

Cardwell et al., "New developments in the treatment of rosacea—role of once-daily ivermectin cream", Clin Cosmetic Invest Dermatol. 2016, 100(9):71-77.

Carmignani et al., 2002, Ophthalmic vehicles containing polymer-solubilized tropicamide: "in vitro/in vivo" evaluation, Drug Development and Industrial Pharmacy, 28(1):101-105.

Carson et al., "*Melaleuca alternifolia* (Tea Tree) Oil: a Review of Antimicrobial and Other Medicinal Properties" Clin Microbiol Rev. 2006, 19(1):50-62.

Casida et al., "Novel GABA receptor pesticide targets", Pest Biochem Physiol. Jun. 2015, (121):22-30.

Casida, "Golden Age of RyR and GABA-R Diamide and Isoxazoline Insecticides: Common Genesis, Serendipity, Surprises, Selectivity, and Safety", Chem Res Toxicol. 2015; 28:560-566.

Casida, "Radioligand Recognition of Insecticide Targets" J. Agric. Food Chem. 2018, 66: pp. 3277-3290.

Cavalleri et al., "A randomised, blinded, controlled field study to assess the efficacy and safety of lotilaner tablets (Credelio™) in controlling fleas in client-owned dogs in European countries" Parasit Vectors. 2017, 10:526 in 8 pages.

Cavalleri et al., "A randomized, controlled study to assess the efficacy and safety of lotilaner (Credelio™) in controlling ticks in client-owned dogs in Europe" Parasit Vectors. 2017, 10:531 in 8 pages.

Cavalleri et al., "Assessment of the onset of lotilaner (Credelio™) speed of kill of fleas on dogs" Parasit Vectors (2017) 10:521 in 5 pages.

Cavalleri et al., "Assessment of the speed of flea kill of lotilaner (Credelio™) throughout the month following oral administration to dogs", Parasit Vectors (2017) 10:529 in 8 pages.

Cavalleri et al., "Laboratory evaluations of the immediate and sustained effectiveness of lotilaner (Credelio™) against three common species of ticks affecting dogs in Europe" Parasit Vectors. 2017, 10:527 in 7 pages.

Cavalleri et al., "Two randomized, controlled studies to assess the efficacy and safety of lotilaner (Credelio™) in preventing *Dermacentor reticulatus* transmission of *Babesia canis* to dogs", Parasit Vectors. 2017, 10:520 in 7 pages.

(56) References Cited

OTHER PUBLICATIONS

Chavez Fernando, "Case Report of Afoxolaner Treatment for Canine Demodicosis in Four Dogs Naturally Infected with Demodex Canis" Intern J Appl Res Vet Med 2016, 14(2):123-127.
Chen et al., "Human demodicosis: revisit and a proposed classification", Br J Dermatol. 2014, 170:1219-1225.
Cheng et al., 2015, Recent advances on ocular Demodex infestation, Current Opinion in Ophthalmology, 26(4):295-300.
Cheung et al., "In vitro anti-demodectic effects and terpinen-4-ol content of commercial eyelid cleansers", Contact Lens Anterior Eye. 2018, 41:513-517.
Chhadva et al., 2017, Meibomian glad disease, American Academy of Ophthalmology, pp. S20-S26.
Chiodini et al., "Parenteral ivermectin in Strongyloides hyperinfection", The Lancet. 2000, 335:43-44.
Clark et al., "Long-term delivery of ivermectin by use of poly(D,L-lactic-co-glycolic)acid microparticles in dogs", AJVR, 2004, 65(6):752-757.
Cliradex® Blepharitis Kit, available at https://cliradex.com/product/cliradex-blepharitis-kit/ (accessed Apr. 4, 2022) 6 pp.
Cliradex® Towelettes Patient Brochure, CX-003 Rev D, Mar. 9, 2016, available at https://cliradex.com/wp-content/uploads/2019/12/cliradex-instructions-for-use.pdf (accessed Apr. 4, 2022) 1 p.
Čolović et al., "Acetylcholinesterase Inhibitors: Pharmacology and Toxicology" Current Neuropharmacology, 2013, 11(3):315-335.
Corta et al., "Kinetics and mechanism of amitraz hydrolysis in aqueous media by HPLC and GC-MS." Talanta. 1999, 48(1):189-99; Abstract in 1 page.
Cosmetic Ingredient Report Expert Panel Meeting (2010). Cosmetic Ingredient Review, 29 total pages.
Costa et al., "Alpha 2-adrenoceptors as a target for formamidine pesticides: in vitro and in vivo studies in mice." Toxicol Appl Pharmacol. 1988, 93(2):319-28, Abstract in 2 pages.
Costa et al., "Ivermectin for spasticity in spinal-cord injury" The Lancet 1994, 343:739.
Cresswell James E., "A meta-analysis of experiments testing the effects of a neonicotinoid insecticide (imidacloprid) on honey bees", Ecotoxicology Nov. 16, 2010 in 9 pages.
Crosaz et al., "Open field study on the efficacy of oral fluralaner for long-term control of flea allergy dermatitis in client-owned dogs in lle-de-France region", Parasit Vectors.. 2016, 9:174 in 5 pages.
Dadzie et al., "Ocular findings in a double-blind study of ivermectin versus diethylcarbamazine versus placebo in the treatment of onchocerciasis", Br J Ophthalmol. 1987, 71:78-85.
De Oliveira et al., "Toxicity effect of the acaricide fipronil in semi-engorged females of the tick *Rhipicephalus sanguineus* (Latreille, 1806) (Acari: Ixodidae): Preliminary determination of the minimum lethal concentration and LC50", Exper Parasitol. 2011, 127:418-422.
De Sole et al., "Adverse reactions after large-scale treatment of onchocerciasis with ivermectin: combined results from eight community trials", WHO Bulletin, 1989, 67(6):707-719.
De Sole et al., "Lack of adverse reactions in ivermectin treatment of onchocerciasis" The Lancet, 1990, 335:1106-1107.
Del Pino et al., "Molecular Mechanisms of Amitraz Mammalian Toxicity: A Comprehensive Review of Existing Data" Chem. Res. Toxicol. 2015, 28:1073-1094.
Do, et al., Setting of ADI for MRLs establishment of insecticide fluxametamide, URL: http://www.dbpia.co.kr/Article/NODE027269043; The 59th Biannual Conference of the Korean Society of Analytical Sciences, Nov. 2017, p. 154 (1 page).
Doan et al., "The efficacy of avermectins (ivermectin, doramectin and abamectin) as treatments for infestation with the tick *Haemaphysalis longicornis* on rabbits in Korea", Vet Parasitol. 2013, 198:406-409.
Dorati et al., "Stability Evaluation of Ivermectin-Loaded Biodegradable Microspheres", AAPS PharmSciTech, 2015, 16(5):1129-1139.

Doshi et al., "Effect of Viscosity, Surface Tension and Mucoadhesion on Ocular Residence Time of Lubricant Eye Drops" Invest Ophthal Visual Science. Apr. 2009, 50:4641; ARVO Annual Meeting Abstract in 2 pages.
Dourmishev et al., "Ivermectin: pharmacology and application in dermatology", Intern J Dermatol. 2005, 44:981-988.
Drugbank, "Levamisole"—Accession No. DB00848 (APRD01067)—DrugBank, 2017, in 10 pages.
DRUGS.com, "Ivermectin", Monograph for Professionals, Am Society of Health-Sys Pharmacists, Inc. [AHFS DI Essentials] 2013, in 19 pages.
DRUGS.com, "Metronidazole", Monograph for Professionals, Am Society of Health-Sys Pharmacists, Inc. [AHFS] 2007 in 36 pages.
Dryden et al., "Evaluation of fluralaner and afoxolaner treatments to control flea populations, reduce pruritus and minimize dermatologic lesions in naturally infested dogs in private residences in west central Florida USA", Parasit Vectors. 2016, 9:365 in 11 pages.
Dryden et al., "Efficacy of fluralaner flavored chews (Bravecto®) administered to dogs against the adult cat flea, Ctenocephalides felis felis and egg production", Parasit Vectors.. 2015, 8:364 in 7 pages.
Durvet, "Ivermectin Injection", Bimeda-MTC Animal Health Inc., Material Safety Data Sheet, Anada 200-447, 2011, in 6 pages.
Durvet, "Ivermectin Sheep Drench", Material Safety Data Sheet, First Priority Inc. Jun. 2, 2002, in 3 pages.
Egeberg et al., "Patients with Rosacea Have Increased Risk of Dementia", Ann Neurol. 2016, 79(6):921-928.0.
Eizadi-Mood et al., "Amitraz Poisoning Treatment: Still Supportive?" Iranian J Pharma Res. 2011, 10(1):155-158.
Elston, "Demodex mites: facts and controversies." Clin Dermatol 2010; 28(5):502-504 [Abstract].
Environmental Protection Agency [EPA], "Amitraz Approval Summary", in 182 pages.
Environmental Protection Agency [EPA], Amitraz R.E.D. Facts Sheet EPA-738-F-96-031, 1996, in 11 pages.
Environmental Protection Agency [EPA], "Carbaryl" Summary (1992): pp. 1-4.
Environmental Protection Agency [EPA], "Fipronil—Environmental Impact Summary for DP Barcode D338854", (2007): pp. 1-71.
Environmental Protection Agency [EPA], Fipronil—New Pesticide Fact Sheet CAS #120068-37-3; (1996): pp. 1-10.
Environmental Protection Agency [EPA], "Margosan-O", Azadirachtin Summary and Registration for Vikwood Ltd. (1984): pp. 1-11.
Erdemir et al., "Demodex mites in acne rosacea: reflectance confocal microscopic study", Australas J Dermatol. 2017, 58(2):e26-e30.
Estermann et al., "Effect of Oral Donepezil on Intraocular Pressure in Normotensive Alzheimer Patients" J Ocular Phama Thera. 2006, 22(1):62-67.
Ethiopia Sheep and Goat Productivity Improvement Program (ESGPIP), "Control of External Parasites of Sheep and Goats" Technical Bulletin No. 41 , 2010: pp. 1-16.
European Medicines Agency [EMA]—Committee for Human Medicinal Products (CHMP/463/00 Rev.1), "Background review for the excipient propylene glycol", Summary of Propylene Glycol Excipient, EMA. Nov. 2014, in 96 pages.
European Medicines Agency [EMA]—Veterinary Medicines and Inspections; "Fluazuron—Summary Report", European Medicines Agency; EMEA/CVMP/77290/05-Final; 2005 in 5 pages.
European Medicines Agency [EMA]—Veterinary Medicines Division, "CVMP assessment report for Bravecto for spot-on solution for dogs and cats (EMEA/V/C/002526/X/0005)"; Mar. 18, 2016: pp. 1-34.
European Medicines Agency [EMA], "European public MRL assessment report (EPMAR)—Fluralaner (poultry)", Feb. 15, 2017: pp. 1-12.
European Medicines Agency [EMA]-Veterinary Medicines Division, "CVMP Assessment Report for NexGard", Committee for Medicinal Products for Veterinary Use (CVMP), Dec. 12, 2013, in 21 pages.
European Medicines Agency [EMA]-Veterinary Medicines Division, "CVMP Assessment Report for Simparica", Committee for Medicinal Products for Veterinary Use (CVMP), Sep. 10, 2015, in 26 pages.

(56) References Cited

OTHER PUBLICATIONS

European Medicines Agency [EMA]-Veterinary Medicines Evaluation Unit, "Cymiazole", Committee for Veterinary Medical Products, Summary Report, Mar. 1996 in 7 pages.
European Union [EU], "Directive 98/8/EC concerning the placing of biocidal products on the market—Imidacloprid", Assessment Report, Feb. 18, 2011, in 131 pages.
Farkouh et al., "Systemic side effects of eye drops: a pharmacokinetic perspective" Clin Ophthalmol. 2016, 10:2433-2441.
FDA Center for Veterinary Medicine, "Animal Drug Safety Communication: FDA Alerts Pet Owners and Veterinarians About Potential for Neurologic Adverse Events Associated with Certain Flea and Tick Products" dated Aug. 5, 2019 and updated Apr. 22, 2019; https://www.fda.gov/animal-veterinary/cvm-updates/animal-drug-safety-communication-fda-alerts-pet-owners-and-veterinarians-about-potential-neurologic (3 pages).
Federal Drug Administration [FDA], "Afoxolaner, Fluralaner and Sarolaner", FDA-CVM FOIA Response 2017-963: pp. 1-26.
Filho et al., "The efficacy of oral ivermectin for the treatment of chronic blepharitis in patients tested positive for Demodex spp.", Br J Ophthalmol. Jun. 2011, 95(6): 893-895.
Fisara et al., "A randomized controlled trial of the efficacy of orally administered fluralaner (Bravecto™) against induced Ixodes holocyclus (Australian paralysis tick) infestations on dogs", Parasit Vectors.. 2015, 8:257 in 6 pages.
Fisara et al., "A small-scale open-label study of the treatment of canine flea allergy dermatitis with fluralaner", Vet Dermatol. 2015, 26: p. 417-e98.
Flajs et al., "Ivermectin Pharmacokinetics", Slov Vet Res 2002; 39(3/4):167-178.
Fluralaner-Bravecto—for veterinary use in Dogs and Cats against fleas and ticks (Jul. 11, 2017), Retrieved from: http://parasilipedia.net/index.php?option=com_content&view=article&id=2731&Itemid=2955, in 3 pages.
Folz et al., "Clinical evaluation of Amitraz as a treatment for canine demodicosis" Vet Parasit. 1984, 16:335-341.
Folz et al., "Evaluation of a topical treatment, alone and in combination with a detergent, for generalized demodicosis" Vet Parasitol., 1984/85, 17:165-172.
Food & Drug Administration [FDA] Veterinary Freedom of Information Summary "Nexgard-Afoxolaner", 2013, in 22 pages.
Food & Drug Administration [FDA], "21-169_Reminyl_medr_P4", 2001, Part 4, Medical Review, retrieved from URL: <.
Food And Drug Administration [FDA], "Bravecto", Freedom of Information Summary NADA 141-426, May 15, 2014; in 39 pages.
Food And Drug Administration [FDA], CFR 21, vol. 5, Part 349 "Ophthalmic Drug Products for over-the-counter human use", [Revised as of Apr. 1, 2016] in 9 pages.
Forton et al., "Demodex folliculorum and topical treatment: acaricidal action evaluated by standardized skin surface biopsy.", Br J Dematol. Mar. 1998, 138(3):461-466 [Abstract].
Foster et al., "Fipronil (Frontline Top Spot)", Information on Use Sheet, etc. in 2 pages.
Foster et al., "The Use of Fipronil (Frontline Top Spot) in Dogs and Cats", from www.peteducation.com in 4 pages.
Foulks et al., [Eds.], "Special Issue—International Dry Eye WorkShop (DEWS) Report", The Ocular Surface, Apr. 2007, 5(2):59-142.
Fourie et al., "Efficacy of a novel formulation of metaflumizone plus amitraz for the treatment of sarcoptic mange in dogs" Vet Parasitol. 2007, 150:275-281.
Fourie et al., "Efficacy of a topical application of Certifect (fipronil 6.26% w/v, amitraz 7.48% w/v, (S)-methoprene 5.63% w/v) for the treatment of canine generalized demodicosis" Parasite 2013, 20:46 in 6 pages.
Fourie et al., "Efficacy of orally administered fluralaner (Bravecto ™) or topically applied imidacloprid/moxidectin (Advocate®) against generalized demodicosis in dogs" Fourie et al. Parasit Vectors., 2015, 8:187 in 7 pages.

Frame et al., "Comparing the in vitro effects of MGO™ Manuka honey and tea tree oil on ocular Demodex viability" Contact Lens Anterior Eye 2018, 41(6):527-530.
G Production Inc., Metrogel® (metronidazole) Gel: Highlights of Prescribing Information in 2 pages.
Galderma Laboratories, LP., "Soolantra™ (ivermectin) cream", Highlights of Prescription Information: Dec. 2014, in 8 pages.
Gao et al., "Clinical Treatment of Ocular Demodicosis by Lid Scrub With Tea Tree Oil", Cornea, Mar. 2007, 26:136-143.
Gao et al., "High Prevalence of Demodex in Eyelashes with Cylindrical Dandruff" Invest Ophthalmol Vis Sci. 2005; 46(9):3089-3094.
Gao et al., "In vitro and in vivo killing of ocular Demodex by tea tree oil" Br J Ophthalmol 2005; 89:1468-1473.
Gardon et al., "Serious reactions after mass treatment of onchocerciasis with ivermectin in an area endemic for Loa loa infection" The Lancet, 1997, 350:18-22.
Gassel et al., "The novel isoxazoline exctoparasiticide fluralaner: Selective inhibition of arthropod γ-aminobutyric acid- and L-glutamate-gated chloride channels and insecticidal/ acaricidal activity", Insect Biochem Mol Biol. 2014; 45:111-124.
Geerling et al., "The International Workshop on Meibomian Gland Dysfunction: Report of the Subcommittee on Management and Treatment of Meibomian Gland Dysfunction", IOVS, Special Issue 2011, 52(4):2050-2064.
Gibbons et al., "A review of the direct and indirect effects of neonicotinoids and fipronil on vertebrate wildlife", Environ Sci Pollut Res. 2015, 22:103-118.
Gonzalez-Salinas et al., Sep. 21, 2021, Safety and efficacy of topical lolitaner ophthalmic solution 0.25% for the treatment of demodex blepharitis: a pilot study, Journal of Ophthalmology, 2021:1-7.
Gordon D.M., "Dimethyl Sulfoxide in Ophthalmology, with Especial Reference to Possible Toxic Effects", Biol Actions of Dimethyl Sulfoxide, 1967, 141:392 in 4 pages.
Government Publishing Office, "Ophthalmic and Topical Dosage Form New Animal Drugs; Ivermectin Topical Solution", 21 CFR Part 524; FR 2011, 76(250):81806-7.
Green-Church et al., "The International Workshop on Meibomian Gland Dysfunction: Report of the Subcommittee on Tear Film Lipids and Lipid-Protein Interactions in Health and Disease" IOVS, Special Issue 2011, 52(4): 1979-1993.
Grubbs Jr. et al., "Instrument Development of the UNC Dry Eye Management Scale", Cornea. Nov. 2014, 33(11):1186-1192.
Gupta et al., "Ivermectin 1% Cream for Rosacea", SkinTherapyLetter. com, Dec. 15, 2015, in 6 pages.
Gupta Ramesh C. [Ed.], "Amitraz", Vet Toxicol. 2007, Chapter 46, pp. 514-517.
Guzzo et al., "Safety, Tolerability, and Pharmacokinetics of Escalating High Doses of Ivermectin in Healthy Adult Subjects", J Clin Pharmacol. 2002, 42:1122-1133.
Hainzl et al., "Mechanisms for Selective Toxicity of Fipronil Insecticide and Its Sulfone Metabolite and Desulfinyl Photoproduct", Chem Res Toxicol. 1998, 11(12):1529-1535.
Halos et al., "Preference of Dogs between Two Commercially Available Oral Formulations of Ectoparasiticide Containing Isoxazolines, Afoxolaner or Fluralaner", Open J Vet Med. 2015, 5:25-29.
Herath et al., "Amitraz poisoning: A case report of an unusual pesticide poisoning in Sri Lanka and literature review" BMC Pharmacol Toxicol. (2017) 18(6):1-6.
Herrero, V.R., "Preservatives in Ophthalmic Formulations: An Overview", Arch Soc Esp Oftalmol. 2007; 82(9):531-532.
Holland et al., "Lifitegrast for the Treatment of Dry Eye Disease—Results of a Phase III Trial (OP3)", Ophthalmol. Jan. 2017, 124(1):53-60.
Holzchuh et al., "Clinical Treatment of Ocular Demodex folliculorum by Systemic Ivermectin" Am J Ophthalmol., 2011, 151:1030-1034.
Hom et al. Randomized Controlled Trial to Evaluate the Safety and Efficacy of TP-03 for the Treatment of Blepharitis Due to Demodex Infestation (Jupiter Study—Phase 2B—Presented at AOA 2020 Virtual Meeting Jun. 26, 2020 available at https://www.tarsusrx.com/jupiter-study (accessed Jul. 13, 2020) in 3 pages.

(56) References Cited

OTHER PUBLICATIONS

Hom et al., "Understanding Emulsion Eye Drop Technology", Rev Optometry. Mar. 2003, 140(3)in 6 pages.
Hosseini et al., "Development and evaluation of a measure of patient-reported symptoms of Blepharitis" Health and Quality of Life Outcomes, 2018, 16:11 in 6 pages.
Inceboz et al., "Diagnosis and Treatment of Demodectic Blepharitis" Türkiye Parazitoloji Dergisi, 2009; 33 (1):p. 32-36.
Intervet Australia Pty Limited, "Bravecto Fluralaner Chewable Tablets for Dogs", Material Safety Data Sheet Feb. 2015, Version 1: pp. 1-11.
Ismailos et al., "Unusual solubility behaviour of cyclosporin A in aqueous media" J Pharm Pharmacol. 1991, 43:287-289.
Jackson Jeremy D., "Infectious folliculitis", UpToDate 2016 (www.uptodate.com) Wolters Kluwer. 2016, in 39 pages.
Jacobi et al., "Demodex Folliculorum in dry eye patients" TFOS 2016 poster in 2 pages.
Jańczak et al., "Clinical aspects of demodicosis in veterinary and human medicine", Med Weter. 2017, 73(5):265-271.
Jarmuda, S. et al. (2012). Potential role of Demodex mites and bacteria in the induction of rosacea, J. Med. Microbial. 61 (Pt. 11):1504-1510.
Jarmuda, S. et al. (2014). "Correlation between serum reactivity to Demodex-associated Bacillusoleronius proteins, and altered sebum levels and Demodex populations in erythematotelangiectaticrosacea patients," J. Med. Microbial. 63(Pt. 2):258-262.
Jelic et al., "Donepezil: A Review of Pharmacological Characteristics and Role in the Management of Alzheimer Disease" Clin Med Insights: Therapeutics 2010, 2:771-788.
Jia et al., "Acute Toxicity, bioconcentration, elimination and antioxidant effects of fluralaner in zebrafish *Danio rerio*", Environ Pollut. 2018, 232:183-190; Epub Sep. 15, 2017.
Jiang et al., "Mosquitocidal Activity and Mode of Action of the Isoxazoline Fluralaner", Int J Environ Res Public Health. 2017, 14:154 in 17 pages.
Johnson, W. (2011). "Safety Assessment of Cyclomethicone, Cyclotetrasiloxane, Cyclopentasiloxane, Cyclohexasiloxane, and Cycloheptasiloxane," International Journal of Toxicology 30(Suppl. 3):149S-227S.
Jon et al., "Liquid matrices for insecticides for "pour on" applications in aqueous medium—Amitraz As A Case Study", in *Pesticide Formulations and Application Systems: Eighteenth Volume*, ASTM STP 1347 [Nalewaja et al.—Eds.] 1998, pp. 228-241.
Jongejan et al., "Comparative efficacy of oral administrated afoxolaner (NexGard™) and fluralaner (Bravecto™) with topically applied permethrin/imidacloprid (Advantix®) against transmission of Ehrlichia canis by infected *Rhipicephalus sanguineus* ticks to dogs", Parasit Vectors. 2016, 9:348 in 14 pages.
Jonsson et al., "Critical evaluation of the modified-adult immersion test with discriminating dose bioassay for Boophilus microplus using American and Australian isolates" Vet Parasitol. 2007, 146:307-315.
Junquera P., "Fluralaner: Safety Summary for Veterinary use in Dogs & Cats (Bravecto)", 2017 in 3 pages.
Kabat Alan G., "In-Vitro Demodicidal Activity of Commercial Lid Hygiene Products" Southern College of Optometry. (2018) Poster in 1 page.
Kagaruki, "The efficacy of amitraz against cattle ticks in Tanzania" Onderstepoort J Vet Res. 1996, 63:91-96.
Karadzovska et al., "A randomized, controlled field study to assess the efficacy and safety of lotilaner flavored chewable tablets (Credelio ™) in eliminating fleas in client-owned dogs in the USA", Parasit Vectors. 2017, 10:528 in 9 pages.
Kaushik et al., "Acetylcholinesterase Inhibitors: Beneficial Effects on Comorbidities in Patients With Alzheimer's Disease" Am J Alzheimers Dis Other Demen. 2018, 33(2):73-85; Epub Oct. 3, 2017 in 13 pages.
Kheirkhah et al., "Fluorescein Dye Improves Microscopic Evaluation and Counting of *Demodex* in Blepharitis With Cylindrical Dandruff" Cornea 2007;26:697-700.

Kilp et al., "Comparative pharmacokinetics of fluralaner in dogs and cats following single topical or intravenous administration", Parasit Vectors. 2016; 9(296) in 7 pages.
Kilp et al., "Pharmacokinetics of fluralaner in dogs following a single oral or intravenous administration" Parasit Vectors 2014, 7:85: pp. 1-5.
Kita et al., "Amitraz and its metabolite differentially activate α- and ⊕-adrenergic-like octopamine receptors." Pest Manag Sci. 2017; 73(5):984-990, Abstract in 2 pages.
Kita et al., "Pharmacological characterization of histamine-gated chloride channels from the housefly *Musca domestica*", NeuroToxicology 60 (2017): pp. 245-253.
Knop et al., "The International Workshop on Meibomian Gland Dysfunction: Report of the Subcommittee on Anatomy, Physiology, and Pathophysiology of the Meibomian Gland", IOVS, Special Issue 2011, 52(4): 1938-1978.
Kojima et al., "In Vivo Evaluation of Ocular Demodicosis Using Laser Scanning Confocal Microscopy", Invest Ophthalmol Visual Science. Jan. 2011, 52(1): 565-569.
Kong et al., "Absolute configuration assignment of (+)-fluralaner using vibrational circular dichroism" Chirality. 2017, 29:854-864.
Kong et al., "Solubility of Imidacloprid in Different Solvents", J Chem Eng Data, 2008, 53:615-618.
Koo et al., "Ocular Surface Discomfort and Demodex: Effect of Tea Tree Oil Eyelid Scrub in Demodex Blepharitis", J Korean Med Sci 2012; 27:1574-1579.
Kugadas et al., "Impact of Microbiome on Ocular Health", The Ocular Surface, Jul. 2016, 14(3):342-349.
Kuntz et al., "Safety evaluation of lotilaner in dogs after oral administration as flavoured chewable tablets (Credelio™)", Parasit Vectors. 2017, 10:538 in 6 pages.
Lacey et al., "Demodex Mites-Commensals, Parasites or Mutualistic Organisms?" Dermatology 2011; 222:128-130.
Lacey et al., "Mite-related bacterial antigens stimulate inflammatory cells in rosacea", Br J Dermatol. 2007, 157(3):474-481.8.
Lacey et al., "Study of Demodex mites: Challenges and Solutions" JEADV 2016, 30:764-775.
Lacey et al., "Under the lash: *Demodex* mites in human diseases" Biochem (Lond) 2009 31(4):2-6.
Laspina et al., "*Demodex* ssp en pacientes con blefaritis crónica", Rev Chilena Infectol 2015; 32(1):37-42.
Lemp et al., "Blepharitis in the United States 2009: A Survey-based Perspective on Prevalence and Treatment" The Ocular Surface, Apr. 2009, 7(2):S1-22.
Lexicomp, Inc. Ivermectin (systemic): Drug information, 2016, in 6 pages.
Li, J. et al. (2010). "Correlation between ocular Demodex infestation and serum immunoreactivity toBacillus proteins in patients with Facial rosacea," Ophthalmology 117:870-877.
Liang et al., "High Prevalence of *Demodex brevis* Infestation in Chalazia" Am J Ophthalmol 2014, 157:342-348.
Lifschitz et al., "Comparative distribution of ivermectin and doramectin to parasite location tissues in cattle", Vet Parasitol. 2000, 87:327-338.
Lilienfeld Sean, "Galantamine—a Novel Cholinergic Drug with a Unique Dual Mode of Action for the Treatment of Patients with Alzheimer's Disease" CNS Drug Reviews, 2002, 8(2):159-176.
Lindsley et al., "Interventions for chronic blepharitis", Cochrane Database Syst Rev. Dec. 2014, 5:e in PMC Dec. 18, 2014, CD005556. doi:10.1002/14651858.CD005556.pub2; in 117 pages.
Little Susan E., "Lotilaner—a novel systemic tick and flea control product for dogs", Parasit Vectors. 2017, 10:539 in 3 pages.
Liu et al., "Pathogenic role of Demodex mites in blepharitis", Curr Opin Allergy Clin Immunol. Oct. 2010, 10(5):505-510.
Lu, G.W., "Recent advances in developing ophthalmic formulations: a patent review", Recent Pat Drug Deliv Formul. Jan. 2010, 4(1):49-57; Abstract in 1 page.
Luntz et al., "Azadirachtin from the Neem Tree Azadirachta indica: its Action Against Insects" An. Soc. Entomol. Brasil. 2000, 29(4):615-632.
Mabrouk ST. The Preparation and Testing of a Common Emulsion and Personal Care Product: Lotion. Journal of Chemical Education vol. 81, No. 1, p. 83-86, 2004. (Year: 2004).

(56) References Cited

OTHER PUBLICATIONS

Maier, "Management of rosacea" UpToDate 2016 (www.uptodate.com), Wolters Kluwer, in 28 pages.
Marie Miglianico, et al., Repurposing isoxazoline veterinary drugs for control of vector-borne human diseases; PNAS; vol. 115, No. 29, pp. E6920-E6926 (6 pages). URL: www.pnas.org/cgi/doi/10.1073/pnas.1801338115.
Marty et al., "Treatment of Human Disseminated Strongyloidiasis with a Parenteral Veterinary Formulation of Ivermectin", Clin Infect Diseases. 2005, 41: e5-8.
Matricoti et al., "The use of oral fluralaner for the treatment of feline generalized demodicosis: a case report" Journal of Small Animal Practice (2017) 58, pp. 476-479.
Mayo Clinic, 2022, Blepharitis, https://www.mayoclinic.org/diseases-conditions/blepharitis/symptoms-causes/syc-20370141.
McKellar et al., "Clinical and pharmacological properties of ivermectin in rabbits and guinea pigs", The Veterinary Record. 1992, 130(4):71-73; Abstract in 2 pages.
McTier et al., "Discovery of sarolaner: A novel, orally administered, broad-spectrum, isoxazoline ectoparasiticide for dogs", Vet Parasitol. 2016, 222:3-11.
Meadows et al., "A randomized, blinded, controlled USA field study to assess the use of fluralaner tablets in controlling canine flea infestations", Parasit Vectors. 2014, 7:375 in 8 pages.
Medisca Inc., "Doxycycline Hyclate USP—Safety Data Sheet", Jul. 2014, in 6 pages.
Medvedev et al., "Clinical-Laboratory Parallels in Patients with Demodectic Blepharitis at Cosmecevtic's Use", Ophthalmology 2015: 12 (4):50-57.
Merck & Co., Inc., "Stromectol® (Ivermectin) Tablets", Prescription Information, May 2010, in 7 pages.
Merck Animal Health, "Compendium of Veterinary Products—Braveclo@ (fluralaner topical solution) for Dogs," dated Aug. 5, 2019: https://merckusa.cvpservice.com/product/basic/view/1047520 (4 pages).
Merck, "Pyrethrins and Synthetic Pyrethroids" Retrieved from: http://www.merckvetmanual.com/pharmacology/ectoparasiticides/ectoparasiticides-used-in-large-animals, downloaded Dec. 11, 2017 in 1 page.
Merial Ltd., "Ivermectin—Ivomec Injection for Cattle and Swine", Material Safety Data Sheet; Jan. 7, 2010, in 7 pages.
Merial Ltd., "NexGard (afoxolaner) Chewables", Safety Data Sheet 2014, in 5 pages.
Merial Ltd., "NexGard (afoxolaner) Chewables", Technical Monograph, 2014, in 21 pages.
Missel et al., "Design and Evaluation of Ophthalmic Pharmaceutical Products", in *Modern Pharmaceutics; 5th Edition* (2009)—Ophthalmic Formulations Guide Chapter 4, pp. 101-189.
Miyajima et al., "Effect of high fat intake on the pharmacokinetic profile of ivermectin in rabbits" Drug Metabolism and Pharmacokinetics 30 (2015): pp. 253-256.
Moser VC., "Amitraz" Encyclopedia of Toxicology, vol. 1, 2014, pp. 200-202.
Mueller et al., "Treatment of canine generalized demodicosis with a 'spot-on' formulation containing 10% moxidectin and 2.5% imidacloprid (Advocate, Bayer Healthcare)", Vet Dermatol. 2009, 20:441-446.
Mueller et al., "Treatment of demodicosis in dogs: 2011 clinical practice guidelines", Vet Dermatol. 2012, 23:86-e21 in 13 pages.
Mueller Ralf S., "Treatment protocols for demodicosis: An evidence-based review", Vet Dermatol. 2004, 15:75-89.
Mullen et al., [Eds.] "Mites (*Acari*)" in *Medical and Veterinary Entomology*, Academic Press, 2009, 2nd Edition, Chapter 26, p. 549.
Mullens et al., "Comparative in vitro evaluation of contact activity of fluralaner, spinosad, phoxim, propoxur, permethrin and deltamethrin against the northern fowl mite, Ornithonyssus sylviarum", Parasit Vectors. 2017; 10:358 in 7 pages.
Murphy et al., "Laboratory evaluations of the immediate and sustained efficacy of lotilaner (Credelio™) against four common species of ticks affecting dogs in North America", Parasit Vectors. 2017, 10:523 in 8 pages.
Murphy et al., 2017, Laboratory evaluation of the speed of kill of lotilaner (Credelio™) against *Ixodes ricinus* ticks on dogs, Parasit Vectors, 10:541, 8 pp.
Narayanan et al., "Use of Carbodiimides as Stabilizing Agents to Deliver Water—Labile Active Ingredients in Liquid Systems Including Aqueous Medium—Amitraz as a Case Study", J ASTM Inter'l., Feb. 2006, 3(2): pp. 1-7.
Nashat et al. "Characterization of Demodex musculi Infestation, Associated Comorbidities, and Topographic Distribution in a Mouse Strain with Defective Adaptive Immunity", Compara Med. 2017, 67(4):315-329.
Nau, Jeffrey. "Oyster Point Pharma", Apr. 12, 2018. PowerPoint in 15 pages.
Nelson et al., "The International Workshop on Meibomian Gland Dysfunction: Report of the Definition and Classification Subcommittee", IOVS, Special Issue. 2011, 52(4):1930-1937.
Ng, Keng Wooi., "Penetration Enhancement of Topical Formulations", Pharmaceutics 2018; 10(51) in 3 pages.
Nicholls et al., "Demodex species in human ocular disease: new clinicopathological aspects." Int Ophthalmol. Epub May 9, 2016, (Abstract) in 2 pages.
Nicholls et al., "Demodex treatment in external ocular disease: the outcomes of a Tasmanian case series", Springer Science+Business Media Dordrecht, Int Ophthalmol. 2016, 6 pages.
Nichols et al., "The International Workshop on Meibomian Gland Dysfunction: Executive Summary", IOVS, Special Issue 2011, 52(4): 1922-1929.
Nichols Kelly K., "The International Workshop on Meibomian Gland Dysfunction: Introduction", IOVS, Special Issue 2011, 52(4):1917-1921.
Ohmes et al., "Comparative Efficacy of an Imidacloprid/Flumethrin Collar (Seresto®) and an Oral Afoxolaner Chewable (NexGard®) against Tick (*Dermacentor variabilis* and *Amblyomma americanum*) Infestations on Dogs: a Randomised Controlled Trial", Parasitol Res. 2015, 114(Suppl 1):S81-94.
Omura et al., "The life and times of ivermectin—a success story", Perspectives, Dec. 2004, 2:984-989.
Ozoe et al., "The antiparasitic isoxazoline443 is a potent blocker of insect ligand-gated chloride channels", Biochem Biophys Res Comm. 2010, 391:744-749.
Pacque et al., "Safety of and compliance with community-based ivermectin therapy", The Lancet, 1990, 335:1377-1380.
Padula et al., "Assessment of the adverse effects of the acaricide amitraz: in vitro evaluation of genotoxicity", Toxicol Mech Methods., 2012; 22(9):657-661.
Palopoli et al., "Global divergence of the human follicle mite *Demodex folliculorum*: Persistent associations between host ancestry and mite lineages" PNAS, Dec. 2015, 112(52):15958-15963.
Panic et al., "Repurposing drugs for the treatment and control of helminth infections", Int J Parasitol Drugs Drug Resist. 2014, 4(3):185-200.
Pass et al., "Pharmacokinetics and metabolism of amitraz in ponies and sheep." J Vet Pharmacol Ther. Jun. 1995; 18(3):210-5, Abstract in 2 pages.
Paterson et al., "Canine generalized demodicosis treated with varying doses of a 2.5% moxidectin + 10% imidacloprid spot-on and oralivermectin: Parasiticidal effects and long-term treatment outcomes", Vet Parasitol. 2014, 205:687-696.
Pathan et al., "Chemical Penetration Enhancers for Transdermal Drug Delivery Systems", Trop J Pharm Res. Apr. 2009; 8 (2):173-179.
PFAU Wolfgang, "Azadirachtin Evaluation of Classification and Labelling Proposal with regard to Developmental Toxicity", Report #234379-A2-050601-01 GAB Consulting GmbH, 2014: pp. 1-15.
Piluli.ru Internet Pharmacy, "Demazol" Instruction Manual, piluli.ru; 2016, in 5 pages.
Powell Frank C., "Rosacea", N Engl J Med. 2005, 352(8):793-803.

(56) References Cited

OTHER PUBLICATIONS

PR Newswire, "Elanco Animal Health Announces U.S. Food and Drug Administration {FDA) Approval of Credelio® {lotilaner) to Treat and Protect Against Ticks and Fleas", PRNewswire, 2018, in 4 pages.

Price et al., "An atypical residue in the pore of Varroa destructor GABA-activated RDL receptors affects picrotoxin block and thymol modulation", Insect Biochem Mol Biol. 2014, 55:19-25.

Prohaczik et al., "Safety of fluralaner oral solution, a novel systemic antiparasitic treatment for chickens, in laying hens after oral administration via drinking water", Parasit Vectors. 2017, 10:363 in 7 pages.

Pubchem, Aug. 2022, Polyoxyl 35 castor oil, CID 154733643, 24 pp.

Puthran et al., "Ivermectin treatment for massive orbital myiasis in an empty socket with concomitant scalp pediculosis", Indian J Ophthalmol. May-Jun. 2012; 60(3):225-227.

Radakovic et al., "Evaluation of the DNA damaging effects of amitraz on human lymphocytes in the Comet assay", J Biosci. 2013, 38(1):53-62.

Rahman M.M., "Synthesis and Structure-Activity Relationships of Iminopyridazine Competitive Antagonists in Insect GABA Receptors", Doctorate Thesis; Tottori University 2014, in 109 pages.

Ramesh et al., "Kinetics and Hydrolysis of Fenamiphos, Fipronil, and Trifluralin in Aqueous Buffer Solutions", J Agric Food Chem. 1999, 47(8):3367-3371.

Richardson Jill A., "Amitraz", Specific Toxicants (2013), Chapter 31, Section 4: pp. 431-433.

Rios-Yu ii, J.M. et al. (2013). "Evaluation of Demodex folliculorum as a Risk Factor for the Diagnosis of Rosacea In Skin Biopsies. Mexico's General Hospital (1975-201 O)," Indian J. Dermatol. 58: 157.

Robinson et al., "Selamectin versus ivermectin for cheyletiellosis in pet rabbits", in *Clinical Decision Making*; Vet Record, 2016, 178:344-346.

Rodriguez-Dehaibes et al., "Resistance to amitraz and flumethrin in *Varroa destructor* populations from Veracruz, Mexico" J Agricult Res. 2007, 44(3):68-69.

Roeder Thomas, "Pharmacology of the octopamine receptor from locust central nervous tissue (OAR3)" Br J Pharmacol. 1995, 114:210-216.

Rohdich et al., "A randomized, blinded, controlled and multi-centered field study comparing the efficacy and safety of Bravecto™ (fluralaner) against Frontline™ (fipronil) in flea- and tick-infested dogs", Parasit Vectors. 2014, 7:83 in 4 pages.

Romero et al., "Efficacy of fluralaner in 17 dogs with sarcoptic mange", Vet Dermatol. 2016, 27:353-e88 in 4 pages.

Roth C. GmbH, "Carvacrol", Safety Data Sheet CAS #499-75-2; (2015): pp. 1-12.

Rufener et al., "The novel isoxazoline ectoparasiticide lotilaner (Credelio™): a non-competitive antagonist specific to invertebrates γ-aminobutyric acid-gated chloride channels (GABACIs)", Parasit Vectors. 2017, 10:530 in 15 pages.

Rufli et al., "The Hair Follicle Mites *Demodex folliculorum* and *Demodex brevis*: Biology and Medical Importance", Dermatologica 1981, 162:1-11.

Rynerson et al., "DEBS—a unification theory for dry eye and blepharitis", Clin Ophthalmol. Dec. 9, 2016, 10:2455-2467.

Sabnis et al., "Topical formulations of metaflumizone plus amitraz to treat flea and tick infestations on dogs", Veterinary Parasitology 150 (2007): pp. 196-202.

Salem, D.A. et al. (2013). "Evaluation of the efficacy of oral ivermectin in comparison with ivermectinmetronidazole combined therapy in the treatment of ocular and skin lesions of Demodex folliculorum,"Int. J. Infect. Dis. 17:e343-e347.

Sánchez-Bayo, "Insecticides Mode of Action in Relation to Their Toxicity to Non-Target Organisms" J Environ Analytic Toxicol. 2011, S4:1-11.

Sanofi Pasteur Inc., "Sklice® (ivermectin) Lotion", Highlights of Prescription Information, Feb. 2012 in 3 pages.

Santana et al., "A novel technique for improving an in vitro culture of *Demodex* spp (Acari: Demodicidae). A pilot trial." Front. Immunol. Conference Abstract: IMMUNOCOLUBIA2015—11th Congress of the Latin American Association of Immunology 2015: 2 pages.

Sattler et al., "Reflectance confocal microscopy for monitoring the density of *Demodex* mites in patients with rosacea before and after treatment", Br J Dermatol. 2015, 173:69-75.

Savla et al., 2020, Tea tree oil for Demodex blepharitis (Review), Cochrane Library, Cochrane Database of Systematic Reviews 2020, Issue 6, Art. No: CD013333, pp. 1-45.

Schaub et al., "Monitoring resistance of pear psylla Cacopsylla pyri to amitraz" Integrated Fruit Production IOBC/wprs Bulletin, 2001, 24(5):151-153.

Schaumberg et al., "Prevalence of Dry Eye Disease Among US Men", Arch Ophthalmol., 2009, 127(6):763-768.

Schaumberg et al., "The International Workshop on Meibomian Gland Dysfunction: Report of the Subcommittee on the Epidemiology of, and Associated Risk Factors for, MGD", IOVS, Special Issue 2011, 52(4):1994-2005.

Schear et al., "The Association of Demodex with Chalazia: A Histopathologic Study of the Eyelid", Ophthal Plast Reconstr Surg. 2016, 32(4):275-278.

Schneider et al., "Metrifonate: A Cholinesterase Inhibitor for Alzheimer's Disease Therapy" CNS Drug Reviews, 1999, 5(1):13-26.

Seddiek et al., "The acaricidal efficacy of aqueous neem extract and ivermectin against Sarcoptes scabiei var. cuniculi in experimentally infested rabbits", Parasitol Res. 2013, 112:2319-2330.

Sedzikowska et al., "Impact of Salvia and Peppermint Oil on the In Vitro Survival of Demodex Mites", J Bacter Parasitol. 2015, 6 (3): in 2 pages.

Sharma et al., "Antihelminthic drugs in recurrent apthous stomatitis: A short review", J Pharm Bioallied Sci. 2014, 6(2):65-68.

Sheng et al., "Insecticidal spectrum of fluralaner to agricultural and sanitary pests", J Asia-Pacific Entomol. 2017, 20:1213-1218.

Shin et al., "Changes in the Eye Microbiota Associated with Contact Lens Wearing", mBio. 2016, 7(2): in 6 pages.

Shoop et al., "Discovery and mode of action of afoxolaner, a new isoxazoline parasiticide for dogs" Vet Parasitol. 2014, 201:179-189.

Shtein et al., "Blepharitis", Official reprint from UpToDate® Wolters Kluwer, Jun. 2016, in 19 pages.

Sigel et al., "Structure, Function, and Modulation of GABAA Receptors", J Biol Chem. 2012, 287(48):40224-40231.

Sigma-Aldrich, "Ivermectin Product Specification", Prod No. 18898 —Sigma-Aldrich.com: 1 page.

Singh et al., "An Update on Therapeutic Management of Canine Demodicosis", Vet World. 2011, 4(1):41-44.

Six et al., "Comparative speed of kill of sarolaner (Simparica™ Chewables) and fluralaner (Bravecto®) against induced infestations of Amblyomma americanum on dogs", Parasit Vectors.. 2016, 9:399 in 7 pages.

Six et al., "Comparative speed of kill of sarolaner (Simparica™) and fluralaner (Bravecto®) against induced infestations of Ctenocephalides felis on dogs" Parasit Vectors., 2016, 9:92 in 7 pages.

Six et al., "Efficacy of sarolaner, a novel oral isoxazoline, against two common mite infestations in dogs: *Demodex* spp. and *Otodectes cynotis*", Vet. Parasitol. 2016, 222:62-66.

Smith et al., "Demodex musculi Infestation in Genetically Immunomodulated Mice", Compara Med. 2016, 66(4):278-285.

Snyder et al., "Efficacy of lotilaner (Credelio™), a novel oral isoxazoline against naturally occurring mange mite infestations in dogs caused by *Demodex* spp." Parasit Vectors. 2017; 10 (532) in 7 pages.

Sojka Peter A., "Therapeutic Review—Isoxazolines", Author's Accepted Manuscript; Journal of Exotic Pet Medicine; 2018: pp. 1-16.

Sudhakar, Chuppani, "Mange in Sheep and Goats" Retrieved from: http://chuppanisudhakar.blogspot.com/2012/02/mange-in-sheep-and-goats.html; Feb. 5, 2012 in 3 pages.

Suntres et al., "The Bioactivity and Toxicological Actions of Carvacrol" Crit Reviews Food Science Nutri. 2015, 55(3):304-318.

Surface Pharmaceuticals Inc. "Corporate Presentation" Nov. 2017, PowerPoint, in 36 pages.

(56) References Cited

OTHER PUBLICATIONS

Szkaradkiewicz et al., "Bacillus oleronius and *Demodex* mite infestation in patients with chronic blepharitis", Clin Microbial Infect 2012, 18:1020-1025; Epub Oct. 22, 2011.

Taenzler et al., "Efficacy of fluralaner administered either orally or topically for the treatment of naturally acquired *Sarcoptes scabiei* var. canis infestation in dogs", Parasit Vectors.. 2016, 9:392 in 5 pages.

Taenzler et al., "Efficacy of fluralaner against Otodectes cynotis infestations in dogs and cats" Parasit Vectors., 2017, 10:30 in 6 pages.

Taenzler et al., "Onset of activity of fluralaner (Bravecto™) against Ctenocephalides felis on dogs" Parasit Vectors.. 2014, 7:567 in 4 pages.

Taenzler et al., "Prevention of transmission of Babesia canis by *Dermacentor reticulatus* ticks to dogs after topical administration of fluralaner spot-on solution" Parasit Vectors, 2016, 9:234 in 3 pages.

Taenzler et al., "Prevention of transmission of Babesia canis by *Dermacentor reticulatus* ticks to dogs treated orally with fluralaner chewable tablets (Bravecto™)", Parasit Vectors. 2015: in 6 pages.

Taenzler et al., "The effect of water and shampooing on the efficacy of fluralaner spot-on solution against Ixodes ricinus and Ctenocephalides felis infestations in dogs", Parasit Vectors, 2016, 9:233 in 5 pages.

Tan et al., "Contemporary Asymmetric Phase Transfer Catalysis: Large-Scale Industrial Applications", Org Process Res Dev. 2015, 19:1731-1746.

Tanrattana C., "Practical and update management of canine demodicosis" Thai J Vet Med Suppl. 2017, 47:S55-S56.

Tantiyaswasdikul, P.S., United Nations Fluazuron Summary Report, 2018, Retrieved from: http://www.fao.org/docrep/w8338e/w8338e09.htm: in 20 pages.

Tarr et al., "Case Report: Rectal Administration of Ivermectin to a Patient with Strongyloides Hyperinfection Syndrome", Am J Trop Med Hyg. 2003, 68(4):453-455.

Tater et al., "Canine and feline demodicosis" DVM Magazine 2008: pp. 1-11.

Taylor-Wells et al., "Variations in the Insect GABA Receptor, RDL, and Their Impact on Receptor Pharmacology", in *Advances in Agrochemicals et al.* by Gross et al. [Eds], ACS Symposium 2017, Chapter 1: pp. 1-21.

Third Party Submission Concise Description of Relevance as Part of A Third-Party Submission Under 37 C.F.R. § 1.290 and 35 U.S.C. 122(E) in related U.S. Appl. No. 16/221,390.

Third-Party Submission under 37 C.F.R. § 1.290 in related U.S. Appl. No. 16/221,390.

Tilley et al. [Eds], "Inflammation of the Eyelids (Blepharitis)" Blackwell's Five-Minute Veterinary Consult: Canine and Feline, Fifth Edition 2011, pp. 1-7.

Tomizawa et al., "Neonicotinoid Insecticide Toxicology: Mechanisms of Selective Action", Annu Rev Pharmacol Toxicol. 2005, 45:247-268.

Tomlinson et al., "The International Workshop on Meibomian Gland Dysfunction: Report of the Diagnosis Subcommittee", IOVS, Special Issue 2011, 52(4): 2006-2049.

Toutain et al., "The intravenous and oral pharmacokinetics of lotilaner in dogs", Parasit Vectors. 2017; 10:522 in 8 pages.

Treatment of Demodex Blepharitis with Ivermectin Gel 0.1 % Plus Metronidazole 1 % (2015). ClinicalTrials.gov, ClinicalTrials.gov Identifier: NCT02236403, 5 total pages.

Türk et al., "Comparison of Incidence of Demodex folliculorum on the Eyelash Follicule in Normal People and Blepharitis Patients", Türkiye Parazitoloji Dergisi, 2007, 31(4):296-297.

U.S. Department of Health & Human Services [HHS], "Toxicological Profile for Pyerethrins and Pyrethroids" Pyerethrins and Pyrethroids, 2003, in 328 pages.

UpToDate; Metronidazole (systemic); Drug information; Woters Kluwer, 2016 in15 pages.

Van Eeden et al., "Solvent and Surfactant Enhanced Solubilization, Stabilization, and Degradation of Amitraz", J Environ Science Health Part B, 2004, B39(1):33-51.

Van Zuuren E.J., "Rosacea", N Engl J Med. 2017, 377(18):1754-1764.

Wall et al., [Eds.] "Chorioptic mange", in *Veterinary Entomology*, Springer Science & Business Media, 1997, p. 341.

Walther et al., "Plasma pharmacokinetic profile of fluralaner (Bravecto™) and ivermectin following concurrent administration to dogs", Parasit Vectors 2015, 8:508 in 5 pages.

Walther et al., "Safety of concurrent treatment of dogs with fluralaner (Bravecto™) and milbemycin oxime—praziquantel", Parasit Vectors 2014, 7:481 in 3 pages.

Walther et al., "Safety of fluralaner chewable tablets (Bravecto™), a novel systemic antiparasitic drug, in dogs after oral administration", Parasit Vectors 2014, 7:87 in 7 pages.

Walther et al., "Safety of fluralaner, a novel systemic antiparasitic drug, in MDR1(–/–) Collies after oral administration", Parasit Vectors 2014, 7:86 in 3 pages.

Walther et al., "Safety of the concurrent treatment of dogs with Bravecto™ (fluralaner) and Scalibor™ protector band (deltamethrin)", Parasit Vectors. 2014, 7:105 in 2 pages.

Walther et al., "The effect of food on the pharmacokinetics of oral fluralaner in dogs", Parasit Vectors. 2014, 7:84: pp. 1-4.

Wang et al., "Direct nucleophilic difluoromethylation of aromatic isoxazoles activated by electron-withdrawing groups using (difluoromethyl) trimethylsilane" ScienceOpen Research (SOR-CHEM) 2014, pp. 1-7.

Watkins, Thomas. "Lessons abound for dermatologists when animal health and human health intersect." 7pp. Sep. 23, 2017. Dermatology News. Available online at: https://www.mdedge.com/dermatology/article/147784/medica-dermatology/lessons-abound-dermatologists-when-animal-health-and.

Weber et al., "Isoxazolines: A Novel Chemotype Highly Effective on Ectoparasites" ChemMedChem 2016, 11:270-276.

Weller Peter F., "Anthelminthic therapies", UpToDate 2016 (www.uptodate.com); Wolters Kluwer, in 5 pages.

Wengenmayer et al., "The speed of kill of fluralaner (Bravecto™) against *Ixodes ricinus* ticks on dogs", Parasit Vectors. 2014, 7:525 in 4 pages.

White et al., "Controlled Trial and Dose-Finding Study of Ivermectin for Treatment of Onchocerciasis", J Infect Diseases, 1987, 156(3):463-470.

Wikipedia, "Demodex folliculorum" Retrieved from: https://en.wikipedia.org/w/index.php?title=Demodex_folliculorum&oldid=727508589, 2016, in 3 pages.

Williams et al., "A quantitative evaluation of the extent of fluralaner uptake by ticks (*Ixodes ricinus, Ixodes scapularis*) in fluralaner (Bravecto™) treated vs. untreated dogs using the parameters tick weight and coxal index", Parasit Vectors. 2015, 8:352 in 8 pages.

Williams et al., "Fluralaner activity against life stages of ticks using Rhipicephalus sanguineus and Ornithodoros moubata IN in vitro contact and feeding assays", Parasit Vectors. 2015; 8(90): 5 pages.

Williams et al., "Fluralaner, a novel isoxazoline, prevents flea (*Ctenocephalides felis*) reproduction in vitro and in a simulated home environment", Parasit Vectors., 2014, 7:275 in 6 pages.

World Health Organization (WHO), "Trichlorfon" International Programme on Chemical Safety (IPCS) 1992: pp. 1-166.

Yeu et al., 2022, Lotilaner ophthalmic solution, 0.25%, for the treatment of demodix blepharitis: results of a prospective, randomized, vehicle-controlled, double-masked, pivotal trial (saturn-1), Cornea, 00:1-9.

Yeu, et al., Safety and Efficacy of Topical Lotilaner 0.25% for the Treatment of Demodex Blepharitis: Results of the Saturn-1 Ph 2b/3 FDA-Pivotal Trial, presented at ASCRS 2021/SPS-107 Ocular Surface, Jul. 24, 2021.

Yilmaz et al., "Amitraz poisoning, an emerging problem: epidemiology, clinical features, management, and preventive strategies" Arch Dis Child 2003; 88: pp. 130-134.

Youngpradej Monchai, "Efficacy of acaricides in controlling broad mite, Polyphagotarsonemus latus (Banks) under laboratory and pot test conditions" Retrieved from : http://agris.fao.org/agris-search/search.do?recordID=TH2000002880; 1998 in 2 pages.

Zegans et al., "Considerations in Understanding the Ocular Surface Microbiome", Am J Ophthalmol. 2014, 158(3):420-422.

(56) References Cited

OTHER PUBLICATIONS

Zelczak Todd A., "Closing the Lid on Blepharitis", PowerPoint, in 41 pages.
Zhang et al., "Discovery of an orally bioavailable isoxazoline benzoxaborole (AN8030) as a long acting animal ectoparasiticide", Bioorg Med Chem Lett. 2015, 25:5589-5593.
Zhang et al., "Optimization of isoxazoline amide benzoxaboroles for identification of a development candidate as an oral long acting animal ectoparasiticide" Bioorganic & Medicinal Chemistry Letters 26 (2016): pp. 3182-3186.
Zhang, Alexis Ceecee, et al., "Ocular Demodex: a systematic review of the clinical literature", Department of Optometry and Vision Sciences, Ophthalmic* Physiological Optics, The Journal of the College of Optometrists, Ophthalmic Physiol Opt 2020, pp. 1-44.
Zhao et al., "Association of Blepharitis with Demodex: A Meta-analysis", Ophthal Epidemiol. 2012, 19(2):95-102.
Zhao et al., "Insect γ-Aminobutyric Acid Receptors and Isoxazoline Insecticides: Toxicological Profiles Relative to the Binding Sites of [$^3$H]Fluralaner, [$^3$H]-4'-Ethynyl-4-n-propylicycloorthobenzoate, and [$^3$H]Avermectin", J Agri. Food Chem. 2014, 62:1019-1024.
Zhao, Y.E. et al. (2012). "A meta-analysis of association between acne vulgaris and Demodex infestation," J. Zhejiang Univ. Sci. B. 13: 192-202.
Zheng et al., "Kinetics and mechanism of the hydrolysis of imidacloprid", Pestic Sci. 1999, 55:482-485.
Zhu et al., "Effect of viscosity on tear drainage and ocular residence time", Optom Vis Sci. Aug. 2008;85(8):715-725; Abstract in 2 pages.
Zoetis U.S., "Terramycin® Ophthalmic Ointment", Patient Order Form downloaded from URL: <https://www.zoetisus.com/products/cats/terramycin-ophthalmic-ointment.aspx.>, in 2 pages.
Zoetis, Revolution Plus® (selamectin and sarolaner topical solution) Prescribing Information, Oct. 2018, available at: https://www.zoetisus.com/_locale-assets/pdf/revolution-plprescribing-information.pdf (accessed Jul. 13, 2020) in 2 pages.
Written Opinion of the International Searching Authority mailed on Oct. 7, 2014, for PCTApplication No. PCT/SG2014/000371, filed on Aug. 4, 2014, 5 pages.—(002 PCT).
International Search Report and Written Opinion for PCT/IB20/53229 mailed on Jul. 29, 2020 in 17 pages.

International Search Report dated Feb. 14, 2019, in related application PCT/US18/65849.
International Search Report mailed on Oct. 7, 2014, for PCT Application No. PCT/SG2014/000371, filed on Aug. 4, 2014, 5 pages.—(002 PCT).
Arita, 2016, Demodex, 33(9):1313-1314.
Cavalleri et al., Jul. 13, 2018, Laboratory evaluation of the efficacy and speed of kill of lotilaner (Credelio™) against *Ixodes ricins* ticks on cats, Parasites & Vectors, 11:413, 10 pp.
CDC, Mar. 30, 2019, Lyme Disease, retrieved from the Wayback Machine on Jan. 26, 2023, https://web.archive.org/web/20190330184401/https://www.cdc.gove/lyme/index.html.
CDC. Diseases Transmitted by Ticks. Retrieved from the internet on May 8, 2023, https://www.cdc.gov/ticks/diseases/index.html#:-:text=Lyme%20disease%20is%20transmitted%20by,pacificus)%20along%20the%20Pacific%20coast. (Year: 2023).
Drugs.com. Credelio (lotilaner). Retrieved from the internet on May 8, 2023, https://www.drugs.com/vet/credelio-lotilaner.html. Published Sep. 2019. (Year: 2019).
Lo Re et al., Apr. 15, 2004, Identifying the vector of lyme disease, Am Fam Physician, 69(8), 3 pp.
Merriam-Webster. Prevent. Retrieved from the internet on May 11, 2023, https://www.merriam-webster.com/dictionary/prevent. (Year:2023).
Sprong et al., Mar. 6, 2018, Control of Lyme borreliosis and other ixodes ricinis-borne diseases, Parasites & Vectors, 11(1):145, 16 pp.
Bandyopadhyay et al., 2010, Development of Ophthalmic formulations, in Nema et al., eds., Pharmaceutical Dosage forms: Parenteral Medications, Third Ed. vol. 1: Formulation and Packing, pp. 255-286.
Kono et al., 2022, State-dependent inhibition of GABA receptor channels by the ectoparasiticide fluralaner, Pesticide Biochemistry and Physiology, 181,:105008.
Lee et al., 2015, Comparison of cytotoxicity and wound healing effect of carboxymethylcellulose and hyaluronic acid on human corneal epithelial cells, Int. J. Ophthalmot. 8(2):215-221.
Pubchem. Fluralaner. Retrieved from the Internet on Aug. 18, 2023.8/23/2 https://pubchem.ncbi.nlm.nih.gov/compound/25144319 (Year:2023).
Holgado et al., 2020, Contact lenses drug-delivery systems: a promising therapeutic tool, Archivos de la Sociedad Espanola de Oftalmologia (English Edition), 95(1):24-33.

* cited by examiner 0.1% amitraz 0.05% and 0.1% fluralaner

ISOXAZOLINE PARASITICIDE FORMULATIONS AND METHODS FOR TREATING BLEPHARITIS

PRIORITY CLAIM

This application claims the benefit under 35 U.S.C. § 120 as a continuation application of U.S. application Ser. No. 17/099,531 filed on Nov. 16, 2020, which in turn claims the benefit under 36 U.S.C. § 120 as a continuation of U.S. application Ser. No. 16/221,390 filed on Dec. 14, 2018, which in turn claims the benefit under 35 U.S.C. § 119(e) as a nonprovisional application of each of U.S. Prov. App. Nos. 62/599,213 filed on Dec. 15, 2017, 62/615,855 filed on Jan. 10, 2018, 62/626,612 filed on Feb. 5, 2018, 62/689,787 filed on Jun. 25, 2018, and 62/746,498 filed on Oct. 16, 2018. Each of the foregoing applications are hereby incorporated by reference in their entireties.

BACKGROUND

Blepharitis, or inflammation of the eyelids, is a common, often chronic condition that can be challenging to treat, and affect any age group. Blepharitis can be both anterior (outer surface of the eyelid affected, where the eyelashes are attached) and/or posterior (inner surface of the eyelid affected). Blepharitis can be associated with systemic diseases including rosacea and seborrheic dermatitis, and be related to other ophthalmic diseases including chalazion, conjunctivitis, keratitis, and dry eyes.

*Demodex folliculorum* and *Demodex brevis* are microscopic, obligate, elongated mites that are the most common permanent intracutaneous parasites inhabiting the hair follicles and sebaceous glands of humans and animals. A total of 65 *Demodex* species have been described, parasitizing 11 orders of mammals and belonging to the family Demodicidae of the order Acarina, class Arachnida. Mating takes place in the follicle opening and eggs are laid inside the hair follicles or sebaceous glands. The six-legged larvae hatch after 3-4 days, and the larvae develop into adults in about 7 days. *Demodex* has a life cycle of about 14 days. The total lifespan of a *Demodex* mite is several weeks. The dead mites decompose inside the hair follicles or sebaceous glands.

*Demodex* can be found on the face, including cheeks, nose, chin, forehead, temples, eye lashes, brows, and also on the scalp, neck, and ears. Other seborrheic locations such as naso-labial folds, peri-orbital areas, and less commonly upper and medial region of chest and back can also be infested. *Demodex* may also be found on the penis, mons veneris, buttocks, and in the ectopic sebaceous glands in the buccal mucosa. In some cases, a mite density of greater than 5 mites/cm$^2$ in the pilo-sebaceous unit or 5 or more mites per follicle correlates with a *Demodex* infestation.

Among a wide range of reported species, only two, *Demodex folliculorum* and *Demodex brevis*, are found to parasitize the human body surface. *Demodex folliculorum* has been found for example on eyelash follicles, while *Demodex brevis* has been found, for example, proximate meibomian (tarsal) glands around the eye and sebaceous glands of the skin. Meibomian glands are a holocrine type of exocrine glands, at the rim of the eyelids inside the tarsal plate, responsible for the supply of meibum, an oily substance that prevents evaporation of the eye's tear film. Meibum prevents tear spillage onto the cheek, trapping tears between the oiled edge and the eyeball, and makes the closed lids airtight. There are approximately 50 glands on the upper eyelids and 25 glands on the lower eyelids. Symbiotic bacteria on the mites also can contribute to pathology. Increased sebum secretion and an increased number of sebaceous glands can provide a favorable habitat for the mites. While some level of *Demodex* can be asymptomatic, multiplication of *Demodex* mites to high densities, and/or a concurrent immune imbalance usually leads to skin damage. A growing body of literature implicates *Demodex* mites in anterior and posterior blepharitis. For example, *Demodex* has been implicated in 45% of blepharitis cases. It has been estimated that the prevalence of ocular surface disease is about 30 million patients; 19 million of which have Meibomian gland dysfunction/posterior blepharitis; 9 million with *Demodex* infestation, and 4 million with clear signs of *Demodex*. Blepharitis is a significant diagnosis, with no approved therapy currently in the US. Safe, efficacious therapies to treat blepharitis and other ophthalmic and dermatologic conditions are needed.

SUMMARY

In some embodiments, disclosed herein are topical therapeutic agents, including but not limited to topical pharmaceutical agents including one or more isoxazoline parasiticides, formamidine parasiticides, phenylpyrazole parasiticides, drugs generally used for the treatment of Alzheimer's disease (e.g., galantamine and others), and other agents for the treatment of various ophthalmic and dermatologic conditions.

In some configurations, disclosed herein is a method for treating blepharitis in a patient, comprising topically administering directly to an ocular surface of one or more eyes of a patient in need of treatment thereof an effective amount of an isoxazoline parasiticide, formulated into an ophthalmic composition, the ophthalmic composition further comprising a pharmaceutically acceptable vehicle.

In some configurations, the ophthalmic composition is sterile and non-irritating to the eye.

In some configurations, the isoxazoline parasiticide can be the sole active ingredient of the ophthalmic composition.

In some configurations, from about 0.01% to about 1% of the isoxazoline parasiticide with respect to the total weight of the composition is administered.

In some configurations, about 0.03% by weight of the isoxazoline parasiticides with respect to the total weight of the composition is administered.

In some configurations, about 0.10% by weight of the isoxazoline parasiticides with respect to the total weight of the composition is administered.

In some configurations, the ophthalmic composition comprises an eye drop.

In some configurations, the ophthalmic composition does not include any essential oils.

In some configurations, the isoxazoline parasiticide is selected from the group consisting of: fluralaner, sarolaner, lotilaner, afoxolaner, and fluxametamide.

In some configurations, the ocular surface comprises at least one of the conjunctiva or cornea of the one or more eyes of the patient.

In some configurations, the ophthalmic composition comprises a polysorbate.

In some configurations, disclosed herein is a method for treating blepharitis in a patient, comprising topically administering directly to one or more of the eye, eyelids, or eyelashes of a patient in need of treatment thereof an effective amount of an isoxazoline parasiticide, formulated into an ophthalmic composition further comprising a pharmaceutically acceptable vehicle, wherein the ophthalmic composition is sterile and non-irritating to the eye, wherein the isoxazoline parasiticide is the sole active ingredient of the ophthalmic composition.

In some configurations, the patient's eyes are closed upon topically administering the ophthalmic composition, such that the composition contacts orifices of Meibomian glands of the patient and outside of eyelid margins of the patient.

In some configurations, the method further comprises spreading the composition onto the eyelashes and follicles of the eyelashes.

In some configurations, the method further comprises spreading the composition onto the eyelashes and follicles of the eyelashes with an applicator.

In some configurations, from about 0.001% to about 1% of the isoxazoline parasiticide is administered.

In some configurations, from about 0.001% to about 1% of the isoxazoline parasiticide is administered.

In some configurations, the method further comprises topically administering the ophthalmic composition at least once daily for at least about 2 weeks.

In some configurations, the method further comprises topically administering the ophthalmic composition at least once daily for at least about 4 weeks.

In some configurations, disclosed herein is a method for treating an ocular *Demodex* infestation in a patient, comprising topically administering directly to one or more of the eyes, eyelids, or eyelashes of one or more eyes of a patient in need of treatment thereof, an effective amount of an isoxazoline parasiticide, formulated into an ophthalmic composition further comprising a pharmaceutically acceptable vehicle, wherein the ophthalmic composition is sterile and non-irritating to the eye, wherein the isoxazoline parasiticide is the sole active ingredient of the ophthalmic composition.

In some configurations, the method further comprises receiving a first assessment of a quantity of *Demodex* mites on an anatomical structure of the patient, and topically administering the ophthalmic composition if the quantity of *Demodex* mites is greater than a predetermined value.

In some configurations, the ophthalmic formulation causes an abdomen and tail of *Demodex* mites on the patient to stop moving more quickly relative to a cephalothorax of the *Demodex* mites.

In some configurations, disclosed herein is a method of treating blepharitis and/or rosacea, comprising topically applying isoxazoline parasiticides proximate one or more eyelashes, the topically applying therapeutically effective to preferentially be absorbed by a body of the *Demodex* mite with respect to ingestion by the *Demodex* mite sufficient to cause reduced movement of the body of the *Demodex* mite with respect to a head of the *Demodex* mite, the method sufficient to reduce or eliminate *Demodex* mites proximate the eyelashes, resulting in improvement of the manifestations of blepharitis and/or rosacea.

In some configurations, disclosed herein is a topical ophthalmic formulation for treating blepharitis in a patient, comprising an effective amount of an isoxazoline parasiticide and a pharmaceutically acceptable vehicle, wherein the ophthalmic composition is sterile and non-irritating to the eye, wherein the isoxazoline parasiticide is the sole active ingredient of the ophthalmic composition.

In some configurations, from about 0.01% to about 1% of the isoxazoline parasiticide with respect to the total weight of the composition is administered.

In some configurations, about 0.03% by weight of the isoxazoline parasiticides with respect to the total weight of the composition is administered.

In some configurations, about 0.10% by weight of the isoxazoline parasiticides with respect to the total weight of the composition is administered.

In some configurations, the ophthalmic composition comprises an eye drop.

In some configurations, the ophthalmic composition does not include any essential oils.

In some configurations, the isoxazoline parasiticide is selected from the group consisting of: fluralaner, sarolaner, lotilaner, afoxolaner, and fluxametamide.

In some configurations, disclosed herein is a topical formulation for use in treating an ocular surface disease, comprising: an isoxazoline parasiticide; at least one of Pemulen and HPMC; polysorbate 80; glycerin; a buffering agent; and lauralkonium chloride, wherein the formulation is therapeutically effective to reduce or eliminate *Demodex* mites proximate the eyelashes, resulting in improvement of the manifestations of blepharitis and/or rosacea.

In some configurations, the formulation is for use in treating blepharitis.

In some configurations, the formulation is for use in treating anterior blepharitis.

In some configurations, the formulation is for use in treating posterior blepharitis.

In some configurations, the formulation is for use in treating ocular rosacea.

In some configurations, disclosed herein is a method for treating blepharitis in a patient, comprising topically administering directly to an ocular surface of one or more eyes of a patient in need of treatment thereof an effective amount of an formamidine parasiticide, formulated into an ophthalmic composition, the ophthalmic composition further comprising a pharmaceutically acceptable vehicle, wherein the ophthalmic composition is sterile and non-irritating to the eye, wherein the formamidine parasiticide is the sole active ingredient of the ophthalmic composition.

In some configurations, from about 0.01% to about 1% of the formamidine parasiticide with respect to the total weight of the composition is administered.

In some configurations, about 0.03% by weight of the formamidine parasiticides with respect to the total weight of the composition is administered.

In some configurations, about 0.10% by weight of the formamidine parasiticides with respect to the total weight of the composition is administered.

In some configurations, the ophthalmic composition comprises an eye drop.

In some configurations, the ophthalmic composition comprises an ointment or cream.

In some configurations, the ophthalmic composition does not include any essential oils.

In some configurations, the formamidine parasiticide is selected from the group consisting of: amitraz, N-(2,4-Dimethylphenyl)-N-methyformamidine (DPMF), and 2,4-dimethylanaline.

In some configurations, the ocular surface comprises at least one of the conjunctiva or cornea of the one or more eyes of the patient.

In some configurations, the ophthalmic composition comprises a polysorbate.

In some configurations, disclosed herein is a method for treating blepharitis in a patient, comprising topically administering directly to one or more of the eye, eyelids, or eyelashes of a patient in need of treatment thereof an effective amount of an formamidine parasiticide, formulated into an ophthalmic composition further comprising a pharmaceutically acceptable vehicle, wherein the ophthalmic composition is sterile and non-irritating to the eye, wherein the formamidine parasiticide is the sole active ingredient of the ophthalmic composition.

In some configurations, the patient's eyes are closed upon topically administering the ophthalmic composition, such that the composition contacts orifices of meibomian glands of the patient and outside of eyelid margins of the patient.

In some configurations, the method further comprises spreading the composition onto the eyelashes and follicles of the eyelashes.

In some configurations, the method further comprises spreading the composition onto the eyelashes and follicles of the eyelashes with an applicator.

In some configurations, from about 0.001% to about 1% of the formamidine parasiticide is administered.

In some configurations, from about 0.001% to about 1% of the formamidine parasiticide is administered.

In some configurations, the method further comprises topically administering the ophthalmic composition at least once daily for at least about 2 weeks.

In some configurations, the method further comprises topically administering the ophthalmic composition at least once daily for at least about 4 weeks.

In some configurations, disclosed herein is a method for treating an ocular *Demodex* infestation in a patient, comprising topically administering directly to one or more of the eyes, eyelids, or eyelashes of one or more eyes of a patient in need of treatment thereof, an effective amount of an formamidine parasiticide, formulated into an ophthalmic composition further comprising a pharmaceutically acceptable vehicle, wherein the ophthalmic composition is sterile and non-irritating to the eye, wherein the formamidine parasiticide is the sole active ingredient of the ophthalmic composition.

In some configurations, the method further comprises receiving a first assessment of a quantity of *Demodex* mites on an anatomical structure of the patient, and topically administering the ophthalmic composition if the quantity of *Demodex* mites is greater than a predetermined value.

In some configurations, the ophthalmic formulation causes an abdomen and tail of *Demodex* mites on the patient to stop moving more quickly relative to a cephalothorax of the *Demodex* mites.

In some configurations, discloses herein is a method of treating blepharitis and/or rosacea, comprising topically applying formamidine parasiticides proximate one or more eyelashes, the topically applying therapeutically effective to preferentially be absorbed by a body of the *Demodex* mite with respect to ingestion by the *Demodex* mite sufficient to cause reduced movement of the body of the *Demodex* mite with respect to a head of the *Demodex* mite, the method sufficient to reduce or eliminate *Demodex* mites proximate the eyelashes, resulting in improvement of the manifestations of blepharitis and/or rosacea.

In some configurations, disclosed herein is a topical ophthalmic formulation for treating blepharitis in a patient, comprising an effective amount of a formamidine parasiticide and a pharmaceutically acceptable vehicle, wherein the ophthalmic composition is sterile and non-irritating to the eye, wherein the formamidine parasiticide is the sole active ingredient of the ophthalmic composition.

In some configurations, from about 0.01% to about 1% of the formamidine parasiticide with respect to the total weight of the composition is administered.

In some configurations, about 0.03% by weight of the formamidine parasiticides with respect to the total weight of the composition is administered.

In some configurations, about 0.10% by weight of the formamidine parasiticides with respect to the total weight of the composition is administered.

In some configurations, the ophthalmic composition comprises an eye drop, a cream, or an ointment.

In some configurations, the ophthalmic composition does not include any essential oils.

In some configurations, the formamidine parasiticide is selected from the group consisting of: amitraz, N-(2,4-Dimethylphenyl)-N-methyformamidine (DPMF), and 2,4-dimethylanaline.

In some configurations, disclosed herein is a method for the treatment of symptoms of blepharitis and/or ocular rosacea in the eye(s), said symptoms being selected from the group consisting of a feeling of burning of the eye, a feeling of smarting of the eye, a feeling of dryness of the eye, an increased sensitivity to light, blurred vision, and a complication of ocular rosacea in the cornea, said method comprising topically administering directly to the conjunctiva and/or to the cornea(s) of the eye(s) of an individual in need of such treatment, a thus effective amount of formamidine parasiticides, formulated into an eyewash composition with a pharmaceutically acceptable vehicle therefor, said eyewash composition being sterile, non-irritating and compatible with eye tissue.

In some configurations, from 0.001% to 10% by weight of formamidine parasiticides with respect to the total weight of the composition is administered.

In some configurations, from 0.01% to 5% of formamidine parasiticides with respect to the total weight of the composition is administered.

In some configurations, 0.03% by weight of formamidine parasiticides with respect to the total weight of the composition is administered.

In some configurations, 0.10% by weight of formamidine parasiticides with respect to the total weight of the composition is administered.

In some configurations, disclosed herein is a method of treating blepharitis and/or rosacea by orally-administering or topically applying formamidine parasiticides in a dosage sufficient to fill and eliminate *Demodex* mites on one or more anatomical locations, resulting in cessation of the manifestations of blepharitis and/or rosacea.

In some configurations, said doses of formamidine parasiticides are repeated about two to four times with spacing of three to seven days between them.

In some configurations, said topically-applied formamidine parasiticides is formulated in a carrier lotion, cream, or gel.

In some configurations, the concentration of formamidine parasiticides in said topically-applied lotion, cream, or gel is about one to five percent by weight.

In some configurations, said topically-applied formamidine parasiticides is applied to eyelids.

In some configurations, said topically-applied formamidine parasiticides is applied to affected skin areas at least once and not more than twice daily for a period of about two to four weeks.

In some configurations, said topically-applied formamidine parasiticides is encapsulated inside microliposomes before being formulated into said carrier lotion, cream, or gel.

In some configurations, disclosed herein is a composition for treating blepharitis and/or rosacea comprising an oral or topical pharmaceutical formulation formamidine parasiticides in a dosage sufficient to eliminate *Demodex* mites on one or more anatomical locations, resulting in cessation of the manifestations of blepharitis and/or rosacea.

In some configurations, disclosed herein is a method for the treatment of cylindrical eyelash dandruff associated with blepharitis and/or ocular rosacea in the eye(s), said method comprising topically administering directly to the conjunctiva and/or to the cornea(s) of the eye(s) of an individual in need of such treatment, a thus effective amount of formamidine parasiticides, formulated into an eyewash composition with a pharmaceutically acceptable vehicle therefor, said eyewash composition being sterile, non-irritating and compatible with eye tissue.

In some configurations, from 0.001% to 10% by weight of formamidine parasiticides with respect to the total weight of the composition is administered.

In some configurations, from 0.01% to 5% of formamidine parasiticides with respect to the total weight of the composition is administered.

In some configurations, 0.03% by weight of formamidine parasiticides with respect to the total weight of the composition is administered.

In some configurations, 0.10% by weight of formamidine parasiticides with respect to the total weight of the composition is administered.

In some configurations, disclosed herein is a method of treating blepharitis and/or rosacea by orally-administering or topically applying formamidine parasiticides in a dosage sufficient to fill and eliminate *Demodex* mites on one or more anatomical locations, resulting in cessation of the manifestations of blepharitis and/or rosacea.

In some configurations, said doses of formamidine parasiticides are repeated about two to four times with spacing of three to seven days between them.

In some configurations, said topically-applied formamidine parasiticides is formulated in a carrier lotion, cream, or gel.

In some configurations, the concentration of formamidine parasiticides in said topically-applied lotion, cream, or gel is about one to five percent by weight, In some configurations, said topically-applied formamidine parasiticides is applied to eyelids.

In some configurations, said topically-applied formamidine parasiticides is applied to affected skin areas at least once and not more than twice daily for a period of about two to four weeks.

In some configurations, said topically-applied formamidine parasiticides is encapsulated inside microliposomes before being formulated into said carrier lotion, cream, or gel.

In some configurations, disclosed herein is a composition for treating blepharitis and/or rosacea comprising an oral or topical pharmaceutical formulation formamidine parasiticides in a dosage sufficient to eliminate *Demodex* mites on one or more anatomical locations, resulting in cessation of the manifestations of blepharitis and/or rosacea.

In some configurations, disclosed herein is a method for the treatment of symptoms of blepharitis and/or ocular rosacea in the eye(s), said symptoms being selected from the group consisting of a feeling of burning of the eye, a feeling of smarting of the eye, a feeling of dryness of the eye, an increased sensitivity to light, blurred vision, and a complication of ocular rosacea in the cornea, said method comprising topically administering directly to the conjunctiva and/or to the cornea(s) of the eye(s) of an individual in need of such treatment, a thus effective amount of formamidine parasiticides, formulated into an eyewash composition with a pharmaceutically acceptable vehicle therefor, said eyewash composition being sterile, non-irritating and compatible with eye tissue.

In some configurations, from 0.001% to 10% by weight of formamidine parasiticides with respect to the total weight of the composition is administered.

In some configurations, from 0.01% to 5% of formamidine parasiticides with respect to the total weight of the composition is administered.

In some configurations, 0.03% by weight of formamidine parasiticides with respect to the total weight of the composition is administered.

In some configurations, 0.10% by weight of formamidine parasiticides with respect to the total weight of the composition is administered.

In some configurations, disclosed herein is a method of treating blepharitis and/or rosacea by orally-administering or topically applying formamidine parasiticides in a dosage sufficient to fill and eliminate *Demodex* mites on one or more anatomical locations, resulting in cessation of the manifestations of blepharitis and/or rosacea.

In some configurations, said doses of formamidine parasiticides are repeated about two to four times with spacing of three to seven days between them.

In some configurations, said topically-applied formamidine parasiticides is formulated in a carrier lotion, cream, or gel.

In some configurations, the concentration of formamidine parasiticides in said topically-applied lotion, cream, or gel is about one to five percent by weight.

In some configurations, said topically-applied formamidine parasiticides is applied to eyelids.

In some configurations, said topically-applied formamidine parasiticides is applied to affected skin areas at least once and not more than twice daily for a period of about two to four weeks.

In some configurations, said topically-applied formamidine parasiticides is encapsulated inside microliposomes before being formulated into said carrier lotion, cream, or gel.

In some configurations, disclosed herein is a composition for treating blepharitis and/or rosacea comprising an oral or topical pharmaceutical formulation formamidine parasiticides in a dosage sufficient to eliminate *Demodex* mites on one or more anatomical locations, resulting in cessation of the manifestations of blepharitis and/or rosacea.

In some configurations, disclosed herein is a method for the treatment of cylindrical eyelash dandruff associated with blepharitis and/or ocular rosacea in the eye(s), said method comprising topically administering directly to the conjunctiva and/or to the cornea(s) of the eye(s) of an individual in need of such treatment, a thus effective amount of formamidine parasiticides, formulated into an eyewash composition with a pharmaceutically acceptable vehicle therefor, said eyewash composition being sterile, non-irritating and compatible with eye tissue.

In some configurations, from 0.001% to 10% by weight of formamidine parasiticides with respect to the total weight of the composition is administered.

In some configurations, from 0.01% to 5% of formamidine parasiticides with respect to the total weight of the composition is administered.

In some configurations, 0.03% by weight of formamidine parasiticides with respect to the total weight of the composition is administered.

In some configurations, 0.10% by weight of formamidine parasiticides with respect to the total weight of the composition is administered.

In some configurations, disclosed herein is a method of treating blepharitis and/or rosacea by orally-administering or topically applying formamidine parasiticides in a dosage sufficient to fill and eliminate *Demodex* mites on one or more anatomical locations, resulting in cessation of the manifestations of blepharitis and/or rosacea.

In some configurations, said doses of formamidine parasiticides are repeated about two to four times with spacing of three to seven days between them.

In some configurations, said topically-applied formamidine parasiticides is formulated in a carrier lotion, cream, or gel.

In some configurations, the concentration of formamidine parasiticides in said topically-applied lotion, cream, or gel is about one to five percent by weight, In some configurations, said topically-applied formamidine parasiticides is applied to eyelids.

In some configurations, said topically-applied formamidine parasiticides is applied to affected skin areas at least once and not more than twice daily for a period of about two to four weeks.

In some configurations, said topically-applied formamidine parasiticides is encapsulated inside microliposomes before being formulated into said carrier lotion, cream, or gel.

In some configurations, disclosed herein is a composition for treating blepharitis and/or rosacea comprising an oral or topical pharmaceutical formulation formamidine parasiticides in a dosage sufficient to eliminate *Demodex* mites on one or more anatomical locations, resulting in cessation of the manifestations of blepharitis and/or rosacea.

In some configurations, disclosed herein is a method for the treatment of symptoms of blepharitis and/or ocular rosacea in the eye(s), said symptoms being selected from the group consisting of a feeling of burning of the eye, a feeling of smarting of the eye, a feeling of dryness of the eye, an increased sensitivity to light, blurred vision, and a complication of ocular rosacea in the cornea, said method comprising topically administering directly to the conjunctiva and/or to the cornea(s) of the eye(s) of an individual in need of such treatment, a thus effective amount of phenylpyrazole parasiticides, formulated into an eyewash composition with a pharmaceutically acceptable vehicle therefor, said eyewash composition being sterile, non-irritating and compatible with eye tissue.

In some configurations, from 0.001% to 10% by weight of phenylpyrazole parasiticides with respect to the total weight of the composition is administered.

In some configurations, from 0.01% to 5% of phenylpyrazole parasiticides with respect to the total weight of the composition is administered.

In some configurations, 0.03% by weight of phenylpyrazole parasiticides with respect to the total weight of the composition is administered.

In some configurations, 0.10% by weight of phenylpyrazole parasiticides with respect to the total weight of the composition is administered.

In some configurations, disclosed herein is a method of treating blepharitis and/or rosacea by orally-administering or topically-applying phenylpyrazole parasiticides in a dosage sufficient to fill and eliminate *Demodex* mites on one or more anatomical locations, resulting in cessation of the manifestations of blepharitis and/or rosacea.

In some configurations, said doses of phenylpyrazole parasiticides are repeated about two to four times with spacing of three to seven days between them.

In some configurations, said topically-applied phenylpyrazole parasiticides is formulated in a carrier lotion, cream, or gel.

In some configurations, the concentration of phenylpyrazole parasiticides in said topically-applied lotion, cream, or gel is about one to five percent by weight.

In some configurations, said topically-applied phenylpyrazole parasiticides is applied to eyelids.

In some configurations, said topically-applied phenylpyrazole parasiticides is applied to affected skin areas at least once and not more than twice daily for a period of about two to four weeks.

In some configurations, said topically-applied phenylpyrazole parasiticides is encapsulated inside microliposomes before being formulated into said carrier lotion, cream, or gel.

In some configurations, disclosed herein is a composition for treating blepharitis and/or rosacea comprising an oral or topical pharmaceutical formulation phenylpyrazole parasiticides in a dosage sufficient to eliminate *Demodex* mites on one or more anatomical locations, resulting in cessation of the manifestations of blepharitis and/or rosacea.

In some configurations, disclosed herein is a method for the treatment of cylindrical eyelash dandruff associated with blepharitis and/or ocular rosacea in the eye(s), said method comprising topically administering directly to the conjunctiva and/or to the cornea(s) of the eye(s) of an individual in need of such treatment, a thus effective amount of phenylpyrazole parasiticides, formulated into an eyewash composition with a pharmaceutically acceptable vehicle therefor, said eyewash composition being sterile, non-irritating and compatible with eye tissue.

In some configurations, from 0.001% to 10% by weight of phenylpyrazole parasiticides with respect to the total weight of the composition is administered.

In some configurations, from 0.01% to 5% of phenylpyrazole parasiticides with respect to the total weight of the composition is administered.

In some configurations, 0.03% by weight of phenylpyrazole parasiticides with respect to the total weight of the composition is administered.

In some configurations, 0.10% by weight of phenylpyrazole parasiticides with respect to the total weight of the composition is administered.

In some configurations, disclosed herein is a method of treating blepharitis and/or rosacea by orally-administering or topically-applying phenylpyrazole parasiticides in a dosage sufficient to fill and eliminate *Demodex* mites on one or more anatomical locations, resulting in cessation of the manifestations of blepharitis and/or rosacea.

In some configurations, said doses of phenylpyrazole parasiticides are repeated about two to four times with spacing of three to seven days between them.

In some configurations, said topically-applied phenylpyrazole parasiticides is formulated in a carrier lotion, cream, or gel.

In some configurations, the concentration of phenylpyrazole parasiticides in said topically-applied lotion, cream, or gel is about one to five percent by weight.

In some configurations, said topically-applied phenylpyrazole parasiticides is applied to eyelids.

In some configurations, said topically-applied phenylpyrazole parasiticides is applied to affected skin areas at least once and not more than twice daily for a period of about two to four weeks.

In some configurations, said topically-applied phenylpyrazole parasiticides is encapsulated inside microliposomes before being formulated into said carrier lotion, cream, or gel.

In some configurations, disclosed herein is a composition for treating blepharitis and/or rosacea comprising an oral or topical pharmaceutical formulation phenylpyrazole parasiticides in a dosage sufficient to eliminate *Demodex* mites on one or more anatomical locations, resulting in cessation of the manifestations of blepharitis and/or rosacea.

In some configurations, disclosed herein is a method for the treatment of symptoms of blepharitis and/or ocular rosacea in the eye(s), said symptoms being selected from the group consisting of a feeling of burning of the eye, a feeling of smarting of the eye, a feeling of dryness of the eye, an increased sensitivity to light, blurred vision, and a complication of ocular rosacea in the cornea, said method comprising topically administering directly to the conjunctiva and/or to the cornea(s) of the eye(s) of an individual in need of such treatment, a thus effective amount of a drug used to treat Alzheimer's disease, formulated into an eyewash composition with a pharmaceutically acceptable vehicle therefor, said eyewash composition being sterile, non-irritating and compatible with eye tissue.

In some configurations, from 0.001% to 10% by weight of drug used to treat Alzheimer's disease with respect to the total weight of the composition is administered.

In some configurations, from 0.01% to 5% of drug used to treat Alzheimer's disease with respect to the total weight of the composition is administered.

In some configurations, 0.03% by weight of drug used to treat Alzheimer's disease with respect to the total weight of the composition is administered.

In some configurations, 0.10% by weight of drug used to treat Alzheimer's disease with respect to the total weight of the composition is administered.

In some configurations, disclosed herein is a method of treating blepharitis and/or rosacea by orally-administering or topically applying drug used to treat Alzheimer's disease in a dosage sufficient to fill and eliminate *Demodex* mites on one or more anatomical locations, resulting in cessation of the manifestations of blepharitis and/or rosacea.

In some configurations, said doses of drug used to treat Alzheimer's disease are repeated about two to four times with spacing of three to seven days between them.

In some configurations, said topically-applied drug used to treat Alzheimer's disease is formulated in a carrier lotion, cream, or gel.

In some configurations, the concentration of drug used to treat Alzheimer's disease in said topically-applied lotion, cream, or gel is about one to five percent by weight.

In some configurations, said topically-applied drug used to treat Alzheimer's disease is applied to eyelids.

In some configurations, said topically-applied drug used to treat Alzheimer's disease is applied to affected skin areas at least once and not more than twice daily for a period of about two to four weeks.

In some configurations, said topically-applied drug used to treat Alzheimer's disease is encapsulated inside microliposomes before being formulated into said carrier lotion, cream, or gel.

In some configurations, disclosed herein is a composition for treating blepharitis and/or rosacea comprising an oral or topical pharmaceutical formulation drug used to treat Alzheimer's disease in a dosage sufficient to eliminate *Demodex* mites on one or more anatomical locations, resulting in cessation of the manifestations of blepharitis and/or rosacea.

DETAILED DESCRIPTION

Figure 1A:
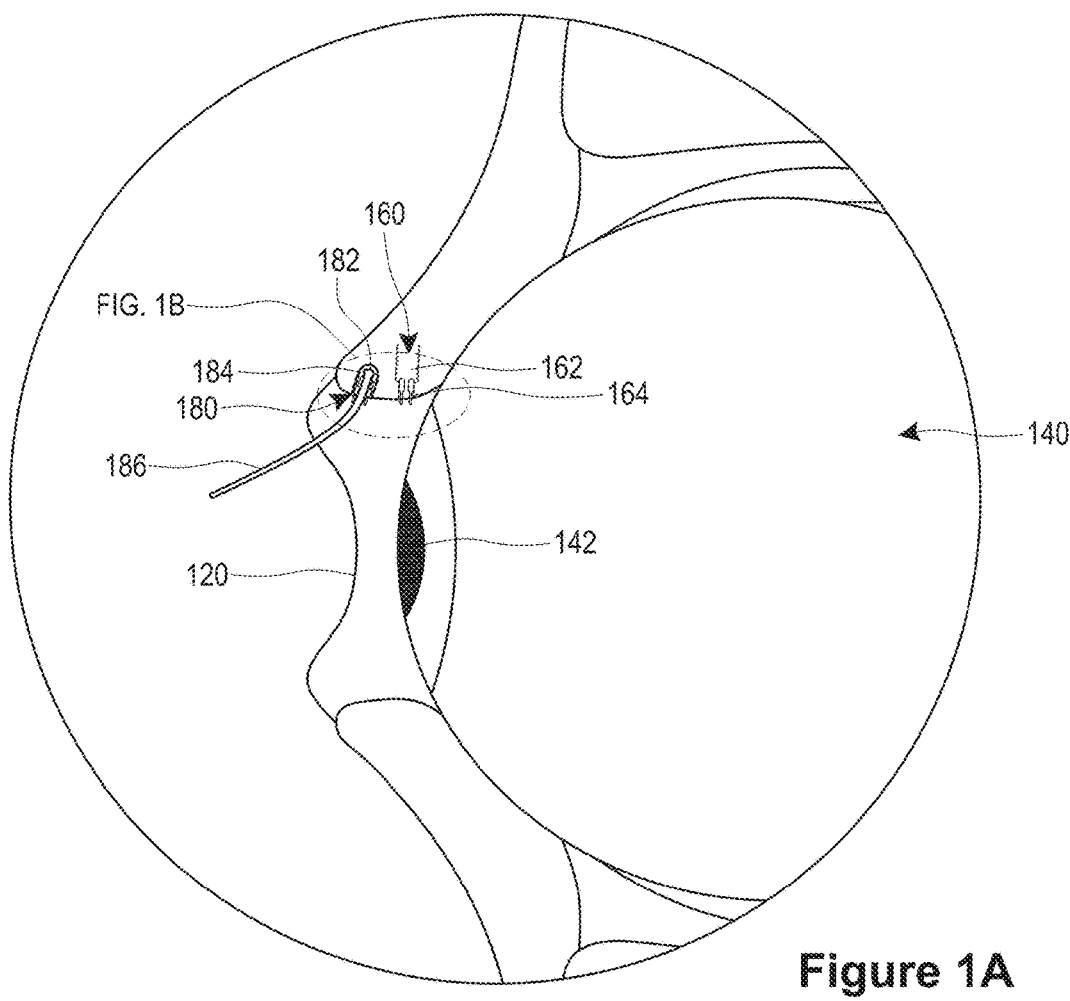
FIGS. 1A-B schematically illustrate application of an ophthalmic formulation onto an eye with a *Demodex* infestation.

In some embodiments, disclosed herein are topical therapeutic agents, including but not limited to topical pharmaceutical agents including one or more isoxazoline parasiticides, formamidine parasiticides, agents used for treating Alzheimer's disease, and other agents as disclosed herein for the treatment of various ophthalmic and dermatologic conditions. Also disclosed herein are methods of treating blepharitis, ocular rosacea, and *Demodex* infestation in patients in need thereof. In some embodiments, patients in need thereof can be treated with an active agent from the isoxazoline parasiticide family of chemicals), which include but are not limited to isoxazoline-substituted benzamide derivatives. Not to be limited by theory, isoxazoline parasiticides can act as GABA-chloride antagonists to selectively target the nervous system of certain organisms, including but not limited to *Demodex*. The GABA-mediated chloride influx can lead to hyperpolarization of the cellular membrane and generates an inhibitory postsynaptic potential, which decreases the probability of an action potential, and lead to paralysis and eventual death of *Demodex* mites. The isoxazoline parasiticide can include, for example, any number of fluralaner, sarolaner, lotilaner, afoxolaner, and/or fluxametamide, including derivatives, analogues, and L- and D-isomers thereof, including but not limited to enantiomers, compositions comprising racemic mixtures, and enantiomerically pure compositions. In some embodiments, the isoxazoline parasiticide, formamidine parasiticide, or other active ingredients as disclosed herein are the only active ingredient utilized in the formulation and/or method. In some embodiments, the isoxazoline parasiticide is an isoxazoline-substituted benzamide derivative. In some embodiments, the isoxazoline parasiticide has one, two, three, or more fluorine groups, such as trifluorine groups in its chemical structure (e.g., $R-CF_3$).

Isoxazoline parasiticides have been conventionally utilized for veterinary applications, including chews and non-ophthalmic topical "pour on" solutions, although to the inventors' knowledge no human formulations have been developed. Non-limiting examples of isoxazoline parasiticides can be found, for example, in U.S. Pat. No. 7,662,972 to Mita et al., U.S. Pat. No. 8,466,115 to Curtis et al., U.S. Pat. No. 7,964,204 to Lahm et al., and U.S. Pat. No. 8,383,659 to Nanchen et al., each of which are hereby incorporated by reference in their entireties. Additionally, U.S. Pub. No. 2010/0254960 A1, PCT Pub. No. WO 2007/

070606 A2, PCT Pub. No. WO 2007/123855 A2, PCT Pub. No. WO 2010/003923 A1, U.S. Pat. Nos. 7,951,828, 7,662,972, U.S. Pub. No. 2010/0137372 A1, U.S. Pub. No. 2010/0179194 A2, U.S. Pub. No. 2011/0086886 A2, U.S. Pub. No. 2011/0059988 A1, US 2010/0179195 A1, PCT Pub. No. WO 2007/075459 A2 and U.S. Pat. No. 7,951,828, all of which are incorporated by reference in their entireties, describe various other parasiticidal isoxazoline compounds. Veterinary oral formulations such as chews result in first pass liver metabolism as well as systemic effects, which can be undesirable in some cases for targeted local applications. A significant challenge is that the fluorinated and/or chlorinated groups of certain isoxazoline parasiticides cause these molecules to be highly insoluble in any pharmaceutical-based solutions including oil and water-based solutions, and having a solubility of less than about 1 mg/kg, or 1 mg/mL aqueous concentrations, or even less. Veterinary topical solutions of isoxazoline parasiticides have included, for example, dimethylacetamide, glycofurol, diethyltoluamide, and/or acetone. However, such solutions are only indicated as a "pour on" solution on the back of the neck of an animal, such as a cat or a dog, are unsuitable for ophthalmic use (and potentially toxic) and include instructions not to administer the solution in or around the eye. Such "pour on" solutions are absorbed systemically by the animal and do not result in targeted local activity only. To the inventors' knowledge, no isoxazoline parasiticides or formamidine parasiticide topical ophthalmic formulations have previously been developed. Therapeutic formulations that are safe and non-toxic for ocular use, and sufficiently soluble to be therapeutically efficacious to treat ocular *Demodex* and related conditions such as blepharitis, for example, are needed.

It has now been determined that compounds of the family of the isoxazoline parasiticides, formamidine parasiticides, agents to treat Alzheimer's disease, and/or other agents as disclosed elsewhere herein can be suitable for the treatment of ophthalmic pathologies of any origin, particularly ophthalmic pathologies due to *Demodex folliculorum*, and more particularly blepharitis and/or ocular rosacea. Other conditions that can be treated via formulations and methods as disclosed herein include, for example, rosacea, *Pityriasis folliculorum*, rosacea-like demodicosis, and demodicosis gravis, nonspecific facial dermatitis, steroid rosacea, androgenetic alopecia, madarosis, lupus miliaris disseminates faciei, dissecting folliculitis, perioral dermatitis, acarica blepharo-conjuncitivitis, papulopustular scalp eruptions, eosinophilic folliculitis, pustular folliculitis, Grover's disease, and *Demodex* abscess.

Ivermectin is another drug that has been used to treat *Demodex*, and is generally more soluble than the isoxazoline parasiticides in solution. However, no known formulations are approved for ocular use (e.g., for blepharitis), and more efficacious therapeutic agents are needed. In some embodiments, a formulation and/or method does not involve an avermectin such as ivermectin or another macrocyclic lactone derivative. However, formulations can include an avermectin in other embodiments.

Disclosed herein are various embodiments of systems, methods, and formulations for the treatment of various eye conditions including but not limited to blepharitis, and the treatment of *Demodex* infestations (e.g., on the eyelid of a subject, such as a human). Embodiments can include any number of features as disclosed herein. Some embodiments do not include dimethylacetamide, glycofurol, diethyltoluamide, and/or acetone, at least some of which can be toxic or irritating to the eye in some cases.

Also disclosed herein is the use of topical isoxazoline parasiticides, formamidine parasiticides, agents to treat Alzheimer's disease, and/or other agents as disclosed elsewhere herein for the treatment of blepharitis and methods of treating *Demodex* infestation and blepharitis in patients in need thereof.

Further disclosed are topical isoxazoline parasiticides, formamidine parasiticides, agents to treat Alzheimer's disease, and/or other agents as disclosed elsewhere herein for the treatment of rosacea and/or ocular rosacea and methods of treating *Demodex* infestation and rosacea and/or ocular rosacea in patients in need thereof (e.g., from the isoxazoline parasiticides family of chemicals). Formulations and methods of reducing *Demodex* mite count proximate the eye of the patient and cylindrical eyelash dandruff are also disclosed.

Also disclosed herein is topical isoxazoline parasiticides, formamidine parasiticides, agents to treat Alzheimer's disease, and/or other agents as disclosed elsewhere herein for the treatment of rosacea and/or ocular rosacea and methods of treating *Demodex* infestation and rosacea and/or ocular rosacea in patients in need thereof.

According to some embodiments, the pharmaceutical composition can include at least one, two, or more compounds selected from the family of the isoxazoline parasiticides including, for example, fluralaner, sarolaner, lotilaner, afoxolaner, and/or fluxametamide, is administered in particular for the treatment of conjunctivitis, blepharitis, ocular rosacea, or other indications including other ocular surface diseases such as meibomian gland dysfunction or dry eye disease.

Some embodiments can include derivatives, analogues, and L- and D-isomers of isoxazoline parasiticides, formamidine parasiticides, or other active therapeutic agents as disclosed elsewhere herein, including but not limited to enantiomers, compositions comprising racemic mixtures, and enantiomerically pure compositions.

In some embodiments, a dose of isoxazoline parasiticides, formamidine parasiticides, agents to treat Alzheimer's disease, and/or other agents as disclosed elsewhere herein can surprisingly be used that is lower than what has been shown to be clinically effective in veterinary medicine, which acts via systemic absorption via topical rinses or washes (e.g., at concentrations in the 1-10 nM, or 100 pM-1 nM range), or ranges including any two of the foregoing values. These lower effective concentrations may be, without limitation, due to direct absorption of drug by the mite body rather than ingestion of drug by the mite, with the abdomen of the mites being thinner (~0.5 um) and more likely to absorb drug than the mites' cephalothorax (~2 um). In some embodiments, direct absorption of drug by the mite body can be the mechanism responsible for at least about 50%, 60%, 70%, 80%, 90%, or more of the total uptake of the drug by the mite.

In some embodiments, daily and local treatment is administered rather than a large long-acting systemic dose (as has been done in veterinary medicine once a month, every 8 weeks, every 12 weeks, every 16 weeks, or less frequently). However, long-acting systemic or local doses could be used in other embodiments.

In some embodiments, dosing could be, for example, about or at least about 1, 2, 3, 4, 5, 6, 7, 8, or more times daily, such as 1 to 2 times daily. In some embodiments, therapy could also be weekly, single dose or a limited-course of treatment. In some embodiments, a formulation can be preferentially used in the morning, at night, or only at night, to target exposure of mites during mating hours.

In some embodiments, formulations can be advantageous in part due to the slow elimination rate of molecules such as isoxazoline parasiticides, however, a small and local dose allows the repeated and frequent dosing, which may be advantageous to disrupt the *Demodex* life cycle through effects on more susceptible juvenile forms, without associated systemic risks and side-effects.

In some embodiments, an active molecule may preferentially be hydrophobic, so it concentrates in regions with either sebum or meibum oils (e.g., eye lash follicles and/or meibomian glands). A formulation may be preferentially water-based to facilitate delivery to and absorption by the hydrophilic chitinous chitosan exterior of *Demodex* mites.

In some embodiments, a therapeutic agent can be delivered in the form of a drop, cream, ointment, eye wash, wipe, salve, or gel, or immediate or sustained release formulation. In some embodiments, a therapeutic agent can be delivered in the form of a punctal or canalicular plug or emulsion. In some cases, a form of an oily, gel-like, viscous ointment may also impede *Demodex* mite movement across the skin surface during mating.

In some embodiments, an isoxazoline parasiticide, formamidine parasiticide, agents to treat Alzheimer's disease, and/or other agents as disclosed elsewhere herein formulation may have preferential selectivity for the receptors of insects/mites/acari over vertebrate/mammalian/human receptors.

In some embodiments, an active agent is delivered in an oral formulation (e.g., tablet, capsule, solution, etc.), and a very small dose may be delivered to avoid meaningful systemic exposure or non-local dermal exposure (in contrast to veterinary teachings). However, in some embodiments, an active agent is delivered in a non-oral formulation, such as a topical formulation, e.g., a topical ophthalmic formulation.

In some embodiments, a dose of between, for example, 1 microgram to 1 mg/ml or 0.0001%-1% active agent (e.g., isoxazoline parasiticides, formamidine parasiticides, agents to treat Alzheimer's disease, and/or other agents as disclosed elsewhere herein) by weight, or between about 0.01% and 10% by weight, between about 0.05% and about 0.5% by weight, or about 0.01%, 0.015%, 0.02%, 0.025%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.00%, or ranges including any two of the aforementioned values, or 1 ng-1 microgram/ml or 0.0000001-0.0001% active agent (e.g., isoxazoline parasiticides, formamidine parasiticides, agents to treat Alzheimer's disease, and/or other agents as disclosed elsewhere herein) by weight, or 1 mg/ml-100 mg/ml or 0.1-10% active agent (e.g., isoxazoline parasiticides, formamidine parasiticides, agents to treat Alzheimer's disease, and/or other agents as disclosed elsewhere herein) by weight, or ranges including any of the foregoing values. In some embodiments, the isoxazoline parasiticides, formamidine parasiticides, agents to treat Alzheimer's disease, or other agents as disclosed elsewhere herein are the only active agent.

In some embodiments, an ophthalmic formulation can be configured for delivery directly onto an ocular surface, including but not limited to the conjunctiva and/or cornea of the eye. In some embodiments, an ophthalmic formulation can be configured for delivery directly or indirectly onto any number of the anterior or posterior eyelids, eye lashes, or eyebrows. In some embodiments, an ophthalmic formulation is not directly delivered to any number of the conjunctiva, cornea, anterior or posterior eyelids, eye lashes, or eyebrows.

An eyedrop formulation may be designed to specifically and simultaneously treat blepharitis and *Demodex* in both the eyelash follicles and/or the meibomian glands, without limitation due to oily additives, emulsions, ointment or cream based formulations, delivery instrument such as lash brushes, or site of application. In some embodiments, a "Drop and Coat the Lashes" (DACTL) technique can be used. A patient can be instructed to close the eye(s) upon administration, thus causing the formulation to come into contact with the orifices of the meibomian glands on the margin(s) of the eyelid, and for the formulation to accumulate outside of the lid margin. The patient can then utilize their finger or an applicator to spread formulation which has accumulated outside of the lid margin onto the eye lashes and/or follicles of the eye lashes on the lower and/or upper eye lashes. Not to be limited by theory, as *Demodex* mites reside in both the eye lash hair follicles and in the meibomian glands, it can be advantageous for the eye drop formulation to be directly applied to one or both of these locations. Since these two targets in combination are unique to this disease, a therapeutic agent can be delivered to these locations simultaneously. The meibomian gland orifices are on the superior and inferior surfaces of the lower and upper eyelids, respectively. An eye drop placed directly onto the ocular surface thus allows for delivery of formulation directly to the upper and lower meibomian gland orifices.

Methods of treating blepharitis and/or *Demodex* infestation can include a formulation/treatment (or similar) delivered specifically by applying a drop in the eye, and then using a finger or instrument (e.g., lash brush) to coat the base of hair follicles in the upper and/or lower eyelids. In some embodiments, desirable features of a formulation can include any number of maximizing drug aqueous solubility to enhance bioavailability (in solution and suspensions), improve the residence time of the drug product in the eye using polymers/viscosity agents, and achieve acceptable visual acuity and comfort.

The viscosity of the formulation may be sufficiently high in some embodiments to cause coverage of formulation over meibomian gland orifices on upper and/or lower lid margins upon blinking or close of the eye.

In some cases, viscosity may be sufficiently high to slow evacuation of formulation through the puncta of the eye for at least 5 seconds, or 10 seconds or 20 seconds or 30 seconds or longer, to enhance contact time of formulation with meibomian gland orifices and to cause the formulation to spill over the lid margin to where it can be accessed for delivery to the eyelash follicles (e.g., by runoff, and/or by spreading of formulation using a finger and/or instrument).

Formulation constituents can be chosen to enable dissolution of active agent into a solution, but with a low concentration by weight of organic solvents, e.g., ≤50%, 20%, 10%, 5%, 2%, or 1%, or less or more by weight organic. This may be achieved at least in part by using a surfactant such as, for example, polysorbate-80 or polysorbate-20. In some cases, low concentrations of polysorbate 80 may be preferentially used, since higher concentrations may lead to isoxazoline parasiticides hydrolysis (e.g., 0.001-0.1% polysorbate 80 by weight).

In some cases, this can also be achieved and solubility of isoxazoline parasiticides enhanced through organic solvents such as propylene glycol.

Solubility and viscosity may be also simultaneously enhanced by selection of an appropriate additive, thereby minimizing osmolarity, e.g., with polyvinyl alcohol, carboxymethylcellulose or the like.

Formulation constituents can be chosen to enable dissolution of active agent (e.g., isoxazoline parasiticides or other active agents) into a solution, and one that is stable from hydrolytic reactions for up to 1, 1.5, 2 years, or more to enable commercial shelf life e.g., with an optimal pH range of neutral to slightly alkaline (e.g., pH 7-10, 7-7.5, or pH 5-7 in other embodiments).

The buffer concentration required to achieve the desired pH can be minimized in some cases, and thus retarding the hydrolysis rate (e.g., phosphate buffer concentration 0.01-0.1M). This may also be achieved with organic solvents and surfactants at concentration ranges described above.

Cationic surfactants, through creation of cationic micelles, can also be advantageous by retarding the hydrolysis rate.

Emulsions and emulsifiers may be mixed with water to shield isoxazoline parasiticides, formamidine parasiticides, agents to treat Alzheimer's disease, and/or other agents and/or other active agents from water in an oil-in-water droplet, e.g., with a carbodiimide additive to prolong stability by forming more complex water-free micelles.

Water scavengers such as Stabaxol I® (bis-2,6-diisopropylphenylcarbodiimide) may be added to achieve long-term oil-based formulations to clean solvents of water.

The pharmaceutical compositions in some embodiments can comprise at least one compound selected from among the family of the isoxazoline parasiticides, formamidine parasiticides, agents to treat Alzheimer's disease, and/or other agents and/or other active agents, are particularly useful for the treatment of ophthalmic symptoms, symptoms selected from a feeling or sensation of burning or of smarting of the eye, a feeling or sensation of a foreign body in the eye, a feeling or sensation of dryness of the eye, an increased sensitivity to light, blurred vision, telangiectasia of the eyelid margin, meibomitis, chalazia, conjunctival hyperemia and papillary conjunctivitis.

The term "treatment" can include treatment in humans and/or other animals.

The pharmaceutical compositions according to some embodiments of the invention can be useful for the treatment of the eyes topically, orally, parenterally or rectally.

The topical application is the most common method of administration of ophthalmic medicaments. The topical route makes possible the instillation into the eye of drops or the application in the eye of solutions, eyewashes, suspensions, salves, ointments, gels, sprays, foams, powders, lotions, viscoelastic solutions and/or the deploying of solid forms at the surface of the eye, impregnated pads, syndets or wipes.

Some formulations can also be provided in the form of suspensions of microspheres or nanospheres or of vesicles formed from lipid or polymer or of polymeric patches and of hydrogels making possible controlled release. These compositions for topical application can be provided in anhydrous form, in aqueous form or in the form of an emulsion.

The pharmaceutical compositions for topical application are preferably non-irritating and compatible with the tissues of the eye. The solutions can be sterile preparations and can be free from all particles. The suspensions can be sterile preparations, and can include solid particles in a liquid vehicle appropriate for ocular instillation. The ointments can be semisolid and sterile preparations.

Orally, the pharmaceutical compositions can be provided in liquid, pasty or solid form, in the form of powders and more particularly in the form of tablets, including sugar-coated tablets, hard gelatin capsules, syrups, suspensions, solutions, powders, granules, emulsions, microspheres or nanospheres or vesicles formed from lipid or polymer making possible controlled release. Parenterally, the compositions can be provided in the form of solutions or suspensions for infusion or for injection. Rectally, the compositions can be provided in the form of suppositories. In some cases, the pharmaceutical compositions are topical ophthalmic compositions, and not oral or rectal compositions.

The compositions can in some embodiments comprise from 0.001% to 10% of at least one compound selected from the family of isoxazoline parasiticides, formamidine parasiticides, agents to treat Alzheimer's disease, and/or other agents as disclosed herein, by weight with respect to the total weight of the composition. In some embodiments, the compositions according to the invention comprise from 0.01% to 5% of at least one compound selected from the family of the isoxazoline parasiticides, by weight with respect to the total weight of the composition.

In some embodiments, the compositions according to the invention are provided in the form of an eyewash or of eye drops. The term "eyewash" means a liquid formulation specifically appropriate for administration to the conjunctiva of the eye and the cornea. The eyewash can include a volume of the instilled drops of, e.g., approximately 25-50 microliters. In some embodiments, compositions are supplied as a kit, for example an eyedrop and shampoo, and may be used along with sterilizing agents such as tea tree oil and derivatives, and hypochlorous acid, which have also been shown to have *Demodex* activity, or not include tea tree or other oils in some cases.

As indicated above, the compositions can in some embodiments meet specific conditions in order to be applied in the eye. Such conditions include, in particular, sterility, absence of irritation and compatibility with the tissues of the eye. The latter criterion is more difficult to obtain than for a composition applied to the skin; in particular, compounds such as ethanol or glycols, formulated in compositions to be applied to the skin, cannot in some cases be included in compositions for ocular use.

The topical compositions can make it possible to directly and specifically treat the symptoms of the pathology in the eye and eyelids by a local action; in particular, since only the eye is targeted, a better effectiveness can be expected.

In some embodiments, a formulation can be in a solution, suspension, cream, ointment, or other form.

A liquid composition, which is formulated for topical ophthalmic use, is formulated such that it can be administered topically to the eye. The comfort may be maximized as much as possible, although sometimes formulation considerations (e.g., drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. These vehicles include, but are not limited to, polyvinyl alcohol, povidone, hydroxypropyl methyl cellulose, poloxamers, carboxymethyl cellulose, hydroxyethyl cellulose and purified water. Ophthalmic solutions may preferably be maintained at a comfortable pH with an appropriate buffer system. The formulations may also contain pharmaceutically acceptable preservatives, stabilizers and surfactants.

In some embodiments, a topical formulation does not include a dermal penetration enhancer, which could increase systemic absorption and be contrary to the intent of maintaining the formulation locally at or proximate the site of application in some cases. In some embodiments, a formulation does not include any dermal penetration enhancers, such as one or more of Laurocapram (Azone®) and laurocapram derivatives, such as 1-alkylazacycloheptan-2-ones, and oleic acid and its ester derivatives, such as methyl, ethyl, propyl, isopropyl, butyl, vinyl and glyceryl monooleate, and sorbitan esters such as sorbitan monolaurate and sorbitan monooleate, and other fatty acid esters such as isopropyl laurate, isopropyl myristate, isopropyl palmitate, diisopropyl adipate, propylene glycol monolaurate and propylene glycol monooleate, and long chain alkyl esters of 2-pyrrolidone, particularly the 1-lauryl, 1-hexyl and 1-(2-ethylhexyl) esters of 2-pyrollidene and those dermal penetration enhancers such as dodecyl (N,N-dimethylamino) acetate and dodecyl (N,N-dimethylamino) propionate and 2-n-nonyl-1-3-dioxolane. However, some embodiments of formulations can include one or more dermal penetration enhancers.

In some embodiments, a topical formulation can include one or more gelling agents. The gelling agent could be a copolymer, such as Pemulen™ TR1 and/or TR2 polymeric emulsifiers (Lubrizol Corp., Wickliffe, OH) which are high molecular weight, copolymers of acrylic acid and C10-C30 alkyl acrylate crosslinked with allyl pentaerythritol. They are fluffy, white powders and are primarily used to form stable oil-in-water emulsions. Pemulen polymers include both hydrophilic and hydrophobic portions within the molecule. The hydrophobic portion of the polymer adsorbs at the oil-water interface, and the hydrophilic portion swells in the water forming a gel network around the oil droplets to provide emulsion stability. Pemulen polymers can form stable oil-in-water emulsions without the need for any additional surfactants. Therefore, they can be advantageous for developing low irritancy lotions and creams, for example. Pemulen polymers provide viscosity building and high yield value to allow for suspension and stabilization of insoluble materials and particulates. In some embodiments, the gelling agent can be absent, or present in the formulation between about 0.001% and about 1%, between about 0.01% and about 0.10%, or about 0.001%, 0.005%, 0.01%, 0.02%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50% w/w of the formulation, or ranges including any two of the foregoing values.

In some embodiments, an oil-based formulation such as a cream, ointment, or emulsion for example can include one or more of mineral oil, castor oil, or petrolatum, such as between about 20% and about 80%, or between about 30% and about 70% w/w of the formulation. The formulation can also include a cyclodextrin as a carrier molecule to facilitate dissolution.

In some embodiments, a topical formulation can include one or more thickening agents, including a polysaccharide thickener, such as hydroxypropylmethylcellulose (HPMC) and sodium CMC. In some embodiments, the thickening agent can be present between about 0% and about 2%, between about 0.10% and about 1.00%, between about 0.25% and about 1.00%, or about 0.10%, 0.20%, 0.25%, 0.30%, 0.35%, 0.40%, 0.50%, 0.60%, 0.70%, 0.80%, 0.90%, 1.00% w/w of the formulation, or ranges including any two of the foregoing values, such as between about 0.1% and about 0.5%. In some embodiments, the formulation can have a viscosity of between about 50 cP and about 100 cP in order to increase the residence time of the formulation in the eye. In some embodiments, a formulation can include a viscosity, for example, of at or above 5 cP or 20 cP or 40 cP or 100 cP or 250 cP or 400 cP or 1000 cP or more, or ranges including any two of the foregoing values. In some cases, the formulation is configured to have a residence time in the eye of between about 90 seconds and about 10 minutes, or about or at least about 60 seconds, 90 seconds, 120 seconds, 180 seconds, 240 seconds, 300 seconds, 6 minutes, 7 minutes, 8 minutes, 9 minutes, 10 minutes, or ranges including any two of the foregoing values.

In some embodiments, a topical formulation can include one or more solubilizer agents and/or surfactants, including a non-ionic surfactant such as a polysorbate, such as Polysorbate 80, Polysorbate 65, Polysorbate 60, Polysorbate 40, or Polysorbate 20. In some embodiments, Polysorbate 80 has been found to unexpectedly result in increased solubility of an isoxazoline parasiticide over other polysorbates. Other surfactants, such as a fluorinated surfactant for example can be substituted or used in addition to a non-ionic surfactant. In some embodiments, the solubilizer agents and/or surfactants can be present between about 0% and about 5%, between about 0.10% and about 4%, between about 0.50% and about 4%, or about 0.50%, 0.75%, 1.00%, 1.25%, 1.50%, 1.75%, 2.00%, 2.25%, 2.50%, 2.75%, 3.00%, 3.25%, 3.50%, 3.75%, 4.00%, 4.25%, 4.50%, 4.75%, 5.00% w/w of the formulation, or ranges including any two of the foregoing values. Polysorbate-80 may also be replaced with Cremphor EL (hydrogenated castor oil) up to FDA monograph limits of 5%, such as about 1%, 2%, 3%, 4%, or 5%, or between about 1% and 5%, or ranges including any two of the aforementioned values, to facilitate higher drug concentrations.

In some embodiments, a formulation (including but not limited to an eye drop, cream, ointment, or other form as disclosed elsewhere herein) can include both a castor oil (e.g., hydrogenated castor oil) and a polysaccharide thickener such as HPMC or sodium CMC. In some cases, the combination can advantageously and unexpectedly form a long-lasting film layer.

In some embodiments, a topical formulation can include one or more tonicity agents, such as glycerin, dextrose, mannitol, potassium chloride, and/or sodium chloride, for example. In some embodiments, the tonicity agent(s) can be present between about 0% and about 5%, between about 0.10% and about 4%, between about 0.50% and about 4%, or about 0.50%, 0.75%, 1.00%, 1.25%, 1.50%, 1.75%, 2.00%, 2.25%, 2.50%, 2.75%, 3.00%, 3.25%, 3.50%, 3.75%, 4.00%, 4.25%, 4.50%, 4.75%, 5.00% w/w of the formulation, or ranges including any two of the foregoing values.

In some embodiments, a topical formulation can include one, two, or more buffering agents. Buffering agents can include, for example, acetate buffers, citrate buffers, phosphate buffers and borate buffers. Acids or bases may be used to adjust the pH of these formulations as needed. The buffering agent could be one or more of sodium bicarbonate buffer, calcium bicarbonate buffer, tris(hydroxymethyl)aminomethane (Tris or THAM), MOPS (3-(N-morpholino)propanesulfonic acid) buffer, HEPES (N-(2-hydroxyethyl)piperazine-N'-(2-ethanesulfonic acid) buffer, ACES (2-[(2-amino-2-oxoethyl)amino]ethanesulfonic acid) buffer, ADA (N-(2-acetamido)-2-iminodiacetic acid) buffer, AMPSO (3-[(1,1-dimethyl-2-hydroxyethyl)amino]-2-propanesulfonic acid) buffer, BES (N,N-bis(2-hydroxyethyl)-2-aminoethanesulfonic acid buffer, Bicine (N,N-bis(2-hydroxyethylglycine) buffer, Bis-Tris (bis-(2-hydroxyethyl)imino-tris(hydroxymethyl)methane buffer, CAPS (3-(cyclohexylamino)-1-propanesulfonic acid) buffer, CAPSO (3-(cyclohexylamino)-2-hydroxy-1-propanesulfonic acid)

buffer, CHES (2-(N-cyclohexylamino)ethanesulfonic acid) buffer, DIPSO (3-[N,N-bis(2-hydroxyethyl)amino]-2-hydroxy-propanesulfonic acid) buffer, HEPPS (N-(2-hydroxyethyl)piperazine)-N'-(3-propanesulfonic acid), buffer, HEPPSO (N-(2-hydroxyethyl)piperazine-N'-(2-hydroxypropanesulfonic acid) buffer, MES (2-(N-morpholino)ethanesulfonic acid) buffer, triethanolamine buffer, imidazole buffer, glycine buffer, ethanolamine buffer, phosphate buffer, MOPSO (3-(N-morpholino)-2-hydroxypropanesulfonic acid) buffer, PIPES (piperazine-N,N'-bis(2-ethanesulfonic acid) buffer, POPSO (piperazine-N,N'-bis(2-hydroxypropanesulfonic acid) buffer; TAPS (N-tris[hydroxymethyl]methyl-3-aminopropanesulfonic acid) buffer, TAPSO (3-[N-tris(hydroxymethyl)methylamino]-2-hydroxy-propanesulfonic acid) buffer, TES (N-tris(hydroxymethyl)methyl-2-aminoethanesulfonic acid) buffer, tricine (N-tris(hydroxymethyl)methylglycine buffer), 2-amino-2-methyl-1,3-propanediol buffer, and 2-amino-2-methyl-1-propanol buffer, as well as combinations thereof. In some embodiments, the buffering agent is Tris and/or disodium hydrogen phosphate ($Na_2HPO_4$) and sodium dihydrogen phosphate heptahydrate ($NaH_2PO_4 7H_2O$). In some embodiments, the buffering agents can be present between about 0% and about 2%, between about 0.01% and about 1%, between about 0.01% and about 0.75%, or about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.20%, 0.25%, 0.30%, 0.35%, 0.40%, 0.45%. 0.50%, 0.55%, 0.60%, 0.65%, 0.70%, 0.75%, 0.80%, 0.85%, 0.90%, 0.95%, 1.00% w/w of the formulation, or ranges including any two of the foregoing values. The buffering agents can be selected in a therapeutically effective amount such that the pH of the pharmaceutical composition can be, for example, between about 7.35 and about 7.65, between about 7.45 and 7.55, or about 7.30, 7.35, 7.40, 7.45, 7.50, 7.55, 7.60, or ranges including any two of the foregoing values.

In some embodiments, a topical formulation can include one or more preservative agents, including but not limited to lauralkonium chloride and benzalkonium chloride. Other preservatives can include, for example, PHMB, chlorobutanol, thimerosal, phenylmercuric, acetate and phenylmercuric nitrate. In some embodiments, the preservative agent can be present in the topical formulation between about 0.001% and about 0.1%, between about 0.001% and about 0.01%, or about 0.001%, 0.002%, 0.003%, 0.004%, 0.005%, 0.006%, 0.007%, 0.008%, 0.009%, 0.010% w/w of the formulation, or ranges including any two of the foregoing values.

The pharmaceutical compositions according to some embodiments of the invention can additionally comprise inert additives or combinations of these additives, such as: wetting agents, emollients; agents for improving flavor; preservatives; stabilizing agents; agents for regulating moisture; pH-regulating agents; buffers; agents for modifying osmotic pressure; emulsifying agents; agents for increasing viscosity; and antioxidants. Ophthalmically acceptable antioxidants include, but are not limited to, sodium metabisulfite, sodium thiosulfate, acetylcysteine, butylated hydroxyanisole and butylated hydroxytoluene. Other excipient components, which may be included in the ophthalmic preparations, are chelating agents. A useful chelating agent is edetate disodium (EDTA), although other chelating agents may also be used in place or in conjunction with it.

In some embodiments, a pharmaceutical composition can include a tocopherol. In some cases, a tocopherol can be effective in preventing degradation of an isoxazoline in water. In some cases, the vitamin E is a tocopherol; in a further embodiment the tocopherol is an alpha- or a gamma-tocopherol; more preferred is an alpha-tocopherol. In some embodiments, a pharmaceutical composition does not include a tocopherol.

In some embodiments, a pharmaceutical formulation does not include any essential oils, such as tea tree oil, alpha-Terpineol, Cardinene, d-Carvone, 1-Carvone, gamma-Terpinene, alpha-Terpinene, 1,8-Cineole, alpha-Terpineol, para-Cimene, alpha-Pinene, Limonene, alpha-Thugene, Eucalyptol, (+)-Ledene, Cuminic Aldehyde, or Myrcene. However, some embodiments can include one or more of the foregoing essential oils.

In some embodiments, optional compound or compounds can be added to these compositions such that the advantageous properties intrinsically associated with some embodiments of the present invention are not, or not substantially, detrimentally affected by the envisaged addition, for example tetracyclines or omega-3 fatty acids, which may have favorable effects in blepharitis.

In some embodiments, an isoxazoline parasiticide is administered orally to a patient with blepharitis, rosacea, or other conditions as disclosed elsewhere herein. Because one target organism, *Demodex folliculorum* (and/or *Demodex brevis*), is an ectoparasite in the mite family, an effective treatment in some cases is therapeutically eradicating the entire life cycle of such a microscopic insect, including egg, larval, and adult stages. For this reason, some embodiments treat blepharitis and/or rosacea patients with at least two doses timed so that between about three and about seven days separate the doses. Such spacing allows time for *Demodex* eggs to hatch into immature mites that are killed before they can mature into egg-producing adults. In some embodiments, 1, 2, 3, 4, or more doses at three- to seven-day intervals could be employed. After an isoxazoline parasiticide or other active agent as disclosed herein carries out its miticidal activity on skin *Demodex folliculorum* organisms (and/or *Demodex brevis* organisms), inflammatory responses to them begin to diminish but remnants of the dead mites still elicit some flushing and lesion formation until the cleanup processes of the body remove them, a process requiring six to eight weeks in some cases. During this initial phase of administration, other medications such as oral tetracycline and topical metronidazole, and/or anti-inflammatory agents such as NSAIDs and/or steroids can be employed to suppress early flareups and to give early clinical response. However, in some embodiments, a formulation or method does not involve a tetracycline or other antibiotic, steroid, and/or metronidazole. After prolonged intervals of freedom from symptoms, should classic signs begin to reappear, treatment can be repeated.

In an alternative embodiment, isoxazoline parasiticides can be formulated into a cosmetically acceptable topical lotion, cream, or gel and applied to skin, eyelids, eyelashes, meibomian glands, or other anatomical locations as noted elsewhere herein. In some cases, such a route of treatment can require once- or twice-daily applications for as long as four weeks to achieve sufficient follicle penetration and effective miticidal activity. A topical formulation that could achieve this effect could contain, for example, about 0.01-5% active ingredient in some cases and could be enhanced in penetration if the active agent were encapsulated inside microliposomes. Such a topical treatment would likely need to be repeated more frequently than the preferred oral embodiment, but a disease-free interval should be achieved by each course of therapy.

Figure 1B:
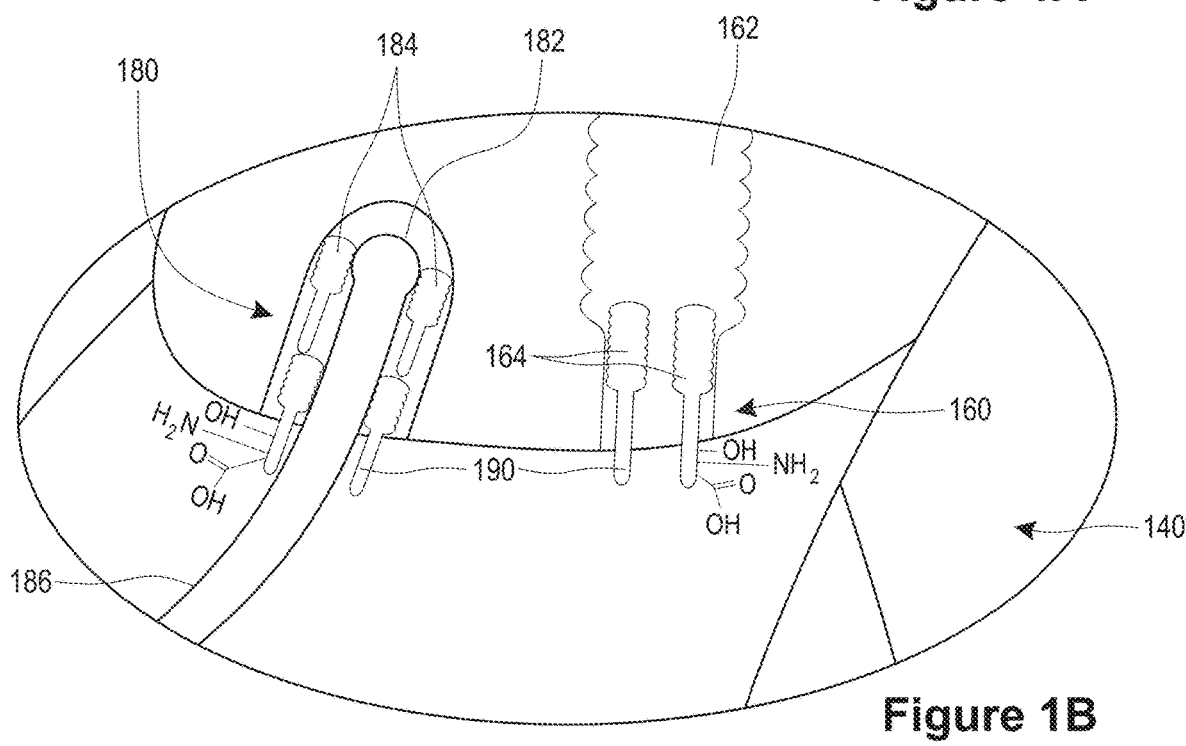
Figure 2:
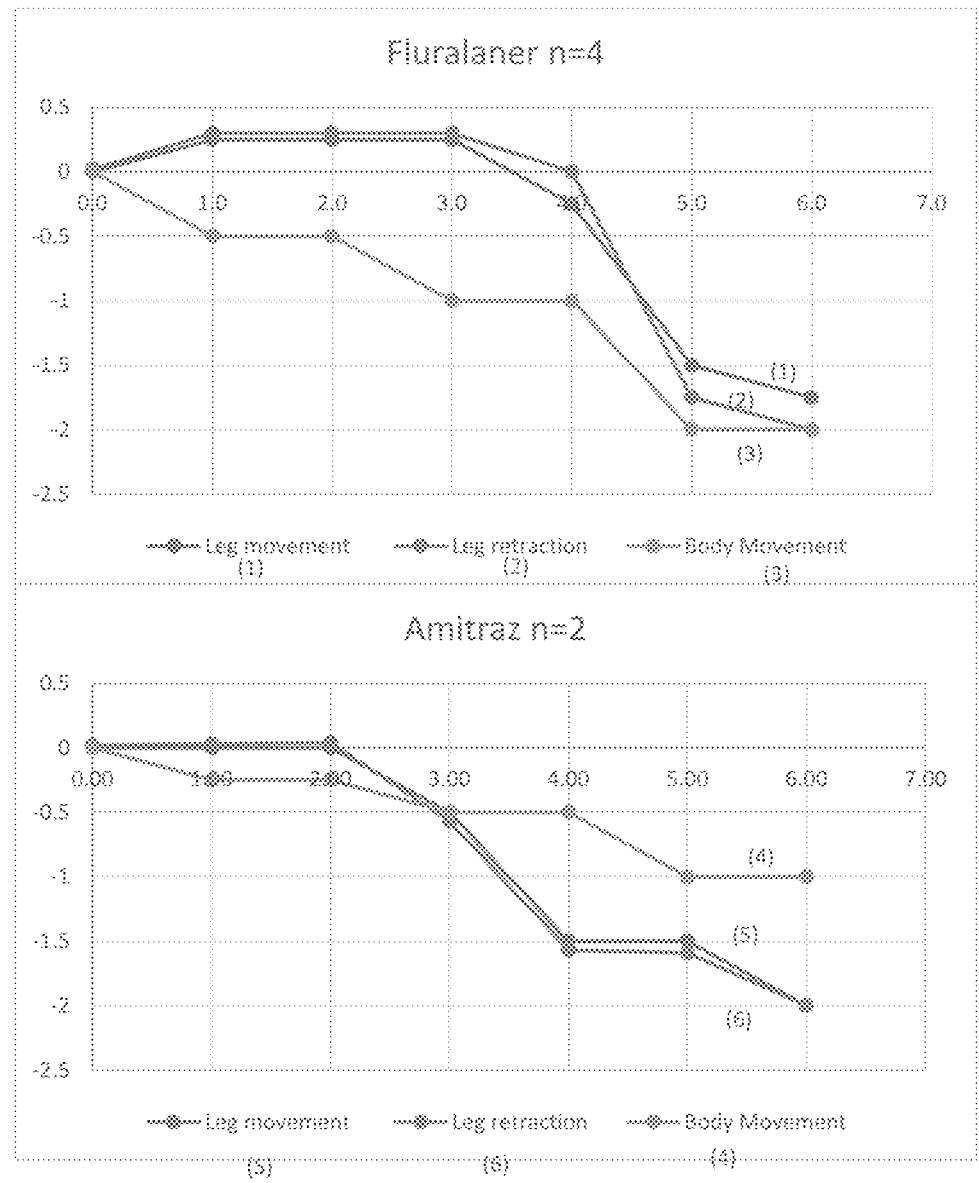
FIG. 2 illustrates data illustrating activity of selected anatomy of *Demodex* mites following therapy with a topical formulation.

In some embodiments, the pharmaceutical formulation including any disclosed herein can be configured to advantageously allow for eradication of the mite proximate an eyelash via preferential absorption of the pharmaceutical formulation through the exoskeleton (e.g., abdomen or opisthosoma) of the mite rather than ingestion of the pharmaceutical formulation by the mite (e.g., by ingesting skin cells, sebum, and other elements that could include an amount of active agent via systemic absorption). Not to be limited by theory, *Demodex* mites have a hydrophobic chitin outer surface, and a relatively thin exoskeleton in the abdomen/opisthosoma area (about 0.5 µm, vs. about 2.0 µm for the cephalothorax portion), which surprisingly has allowed for more rapid absorption of the formulation through the abdomen, instead of primarily via ingestion as in previous veterinary formulations of isoxazoline parasiticides. FIGS. 1A-B schematically illustrate application of a formulation 120 onto an eye 140 with an iris/pupil 142. An eyelid around the eye 140 may include a hair follicle 180 for an eyelash 186 and the follicle 180 may include sebum oil 182. The eyelid may include a meibomian gland 160 with meibum oil 162. As shown in FIGS. 1A-B, a "face down" orientation of the mites (e.g., *Demodex folliculorum* 164, *Demodex brevis* 184) with respect to the hair follicle 180 or a Meibomian gland 160 (with the mite body pointing to the opening of the follicle 180 or the gland 160) may facilitate the preferential abdominal absorption of the formulation 120 through abdomen/opisthosoma area 190. In ex vivo studies, it has been surprisingly observed that following delivery of certain pharmaceutical formulations as disclosed herein that the abdomen and tail portion of a *Demodex* mite stops moving more quickly than the cephalothorax as in FIG. 2, indicating *Demodex* mites are especially susceptible to topical ophthalmic formulations as disclosed herein.

In some embodiments, compositions and methods as disclosed herein can be used alone or in combination with any number of the following agents, in topical or other forms, which can be made into formulations having parameters including any features including but not limited to concentrations, excipients, and other features or absence of other features as disclosed elsewhere herein: albendazole, cambendazole, fenbendazole, flubendazole, mebendazole, oxfendazole, parbendazole, thiabendazole, triclabendazole, amitraz, demiditraz, clorsulon, closantel, oxyclozanide, rafoxanide, cyphenothrin, flumethrin, permethrin, promazine, derquantel, diamphenethide, dicyclanil, dinotefuran, imidacloprid, nitenpyram, thiamethoxam, abamectin, doramectin, emamectin, eprinomectin, ivermectin, moxidectin, selamectin, milbemycin oxime, emodepside, epsiprantel, fipronil, fluazuron, fluhexafon, indoxacarb, levamisole, lufenuron, metaflumizone, methoprene, monepantel, morantel, niclosamide, nitroscanate, nitroxynil, novaluron, oxantel, praziquantel, pyrantel, pyriprole, pvriproxyfen, sisapronil, spinosad, spinetoram, lindane, picrotoxin, dieldrin, alpha-endosulfan, and/or triflumezopyrim. In some embodiments, compositions and methods can include a meta-diamide (e.g., broflanilide), a cyclodiene, and/or a macro-cyclic lactone (including avermectins and milbemycin). In some embodiments, an Alzheimer's disease drug can be the active agent, such as galantamine, donepezil and other piperidine analogues, rivastigmine and other carbamate analogues, tacrine, 7-methoxytacrine, other pyridine analogues, huperzine A and other alkaloid analogues, which can also have anti-*Demodex* activity. Galantamine for example is a selective, competitive rapidly reversible acetylcholinesterase inhibitor with the anionic substrate and aromatic gorge, and an allosteric ligand/activator at the nicotinic cholinergic receptors, thus increasing GABA activity. Other acetylcholinesterase inhibitors could be utilized as well in some cases. Derivatives, analogues, and L- and D-isomers thereof, including but not limited to enantiomers, compositions comprising racemic mixtures, and enantiomerically pure compositions of any of the foregoing in this paragraph can also be utilized. In some embodiments, a formulation does not include any number of, or all of the agents listed in this paragraph.

In some embodiments, a dermatologic and/or ophthalmologic formulation can include an active therapeutic agent of a formamidine parasiticide instead of, or in addition to an isoxazoline parasiticide as disclosed above. A formamidine parasiticide can be, for example, amitraz, which can function as an octopamine receptor modulator. N-(2,4-Dimethylphenyl)-N-methyformamidine (DPMF), a metabolite of amitraz, is thought to be an active agent that exerts acaricidal and insecticidal effects by acting as an agonist on octopamine receptors, and can be another active therapeutic agent, alone or in addition. 2,4-dimethylanaline is a hydrolysis metabolite of DPMF and can also be an active therapeutic agent in other embodiments. Derivatives, analogues, and L- and D-isomers thereof, including but not limited to enantiomers, compositions comprising racemic mixtures, and enantiomerically pure compositions can also be utilized. In some embodiments, a dermatologic and/or ophthalmologic formulation can include an active therapeutic agent of a phenylpyrazole parasiticide instead of, or in addition to an isoxazoline or formamidine parasiticide as disclosed above. The chemical structures of these insecticides are characterized by a central pyrazole ring with a phenyl group attached to one of the nitrogen atoms of the pyrazole. Some non-limiting examples of phenyl pyrazole parasiticides include, for example, acetoprole, ethiprole, fipronil, flufiprole, pyraclofos, pyrafluprole, pyriprole, pyrolan, and vaniliprole.

Figure 3A:
FIGS. 3A-3B show examples of formulations with amitraz and fluralaner.
Figure 3B:

To further illustrate some embodiments and advantages thereof, Table 1 below lists several non-limiting specific examples of topical isoxazoline parasiticide formulations for illustrative purposes only. All ingredients are listed as % w/w or grams/100 grams of preparation, and FIGS. 3A-3B shows examples of formulations with amitraz and fluralaner.

One example embodiment of an amitraz solution includes 0.100% w/w of Amitraz in 99.9% light mineral oil. Another example of an amitraz ointment can include 0.100% w/w of Amitraz and 29.9% mineral oil and 70.0% petrolatum.

TABLE 1

| Ingredient | Solution 1 | Solution 2 | Suspension 1 |
| --- | --- | --- | --- |
| Fluralaner | 0.0100 | 0.0250 | 0.500 |
| Pemulen TR1 | 0 | 0 | 0.050 |
| HPMC | 0.50 | 0.50 | 0 |
| Polysorbate 80 | 2.0 | 2.0 | 2.0 |
| Glycerin | 2.5 | 2.5 | 2.5 |
| TRIS | 0 | 0 | 0.050 |
| $NaH_2PO_4 7H_2O$ | 0.44 | 0.44 | 0 |
| $Na_2HPO_4$ | 0.045 | 0.045 | 0 |
| pH | 7.5 | 7.5 | 7.5 |
| Lauralkonium Chloride | 0.0050 | 0.0050 | 0.0050 |
| Water | q.s. ad 100% | q.s. ad 100% | q.s. ad 100% |

In some embodiments, a topical ophthalmic formulation can include the following instructions for use. A patient can be instructed to shower or bathe first before applying the study medication and to wash their hands before applying the study medication. A unit dose, such as a single drop of the formulation can be directly applied into each eye once or twice a day, e.g., once in the morning and once in the evening. After delivering the drop to the conjunctiva and/or cornea of the eye, the patient can close their eyes and apply gentle pressure to the upper lid to express the medication across their upper and lower eyelid margins. The formulation can then be allowed to dry without dabbing with a tissue. The formulation can then be stored at room temperature in a climate-controlled environment (15 to 30° C.), avoiding extreme heat or cold. In some embodiments, the patient is instructed not to apply any other topical ophthalmic medications within a specified period, e.g., one hour before and one hour after administering the study medication.

In some embodiments, systems and methods include qualitative and/or quantitative assessment of *Demodex* on an anatomical location of the patient, such as on eyelashes and/or within glands, for example. In some embodiments, a method can include receiving a first assessment of a quantity of *Demodex* mites on an anatomical structure of the patient and initiating topical administration of the dermatologic and/or ophthalmic composition if the quantity of *Demodex* mites is greater than a predetermined value, such as greater than about 1, 1.5, 2, 2.5, 3, 4, 5, or more mites per square centimeter of skin (or mites per lash). In some embodiments, a method can include receiving a second assessment of a quantity of *Demodex* mites following therapy to quantitatively assess improvement, and either continuing, modifying (via an increase or decrease in dose, frequency, formulation, and the like), or discontinuing therapy based on the second assessment, which can be about, no more than about, or at least about 1 day, 2 days, 3 days, 5 days, 7 days, 10 days, 14 days, 21 days, 28 days, 30 days, or more or less after the first assessment. In some embodiments, the therapy results in a reduction of about or at least about 10%, 20%, 30%, 40%, 50%, 60%, 70%, 80%, 90%, or 100% eradication of the *Demodex* at the anatomic location.

The presence of cylindrical dandruff, also known as cylindrical casts, are scales that form clear cuffs collaring the eyelash root, at the base of the eyelash. Cylindrical dandruff on an eyelash is generally considered pathognomonic for *Demodex* infestation, can be diagnosed via epilation and viewed under a slit lamp microscope, and then counted automatically or manually. Skin surface biopsy (SSB) technique with cyanoacrylic adhesion is a commonly used method to measure the density of *Demodex*. It allows the collection of the superficial part of the horny layer and the contents of the pilo-sebaceous follicle. Other sampling methods used in assessing the presence of *Demodex* by microscopy include adhesive bands, skin scrapings, skin impressions, expressed follicular contents, comedone extraction, hair epilation, and punch biopsies.

In some embodiments, systems and methods for detecting *Demodex* in a subject are disclosed that do not necessarily require epilation. Such measures of diagnosis of *Demodex* can be advantageous because *Demodex*, particularly *Demodex brevis* can be challenging to detect and quantify via epilation. Furthermore, many patients object to epilation due to discomfort. Furthermore, initiation of treatment could be earlier and based on objective criteria.

For example, a device, such as a disposable hydrogel contact lens can be utilized to collect tears from a subject. This device, e.g., lens is then sent to a laboratory for detecting, and potentially quantifying, *Demodex* DNA by PCR or other means. The genome for both *Demodex folliculorum* and *Demodex brevis* have been sequenced. A "diagnostic" lens can be placed on the eye and removed after at a short, fixed period, such as about or less than about 30, 20, 15, 10, or 5 minutes, for example. Such a lens can made of a hydrogel with relatively high affinity for a *Demodex* biomarker, including DNA.

Figure 4A:
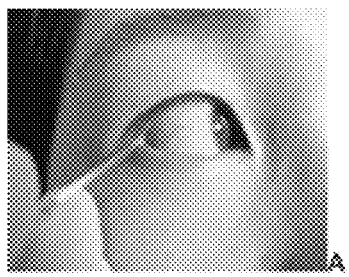
FIGS. 4A-4C illustrate embodiments of various diagnostic techniques for *Demodex* that do not necessarily require epilation.

In some embodiments, tear sampling can utilize devices including capillary glass tubes to harvest tears from the lower lid tear meniscus as shown in FIG. 4A. This method can be especially useful when quantitative, small volumes are needed. In addition, evaporation can be eliminated, if beneficial to do so, simply by sealing both ends of the tube.

Figure 4B:
Figure 4C:
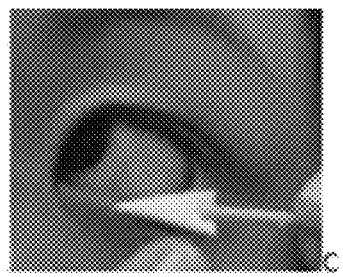

Some embodiments also include non-contact lens skin and tear sampling methods, for example a "litmus paper" or wicking paper embodiment similar to a Schirmer test (illustrated in FIG. 4B), or a lash brush harvesting technique (illustrated in FIG. 4C). In some embodiments, chitin, chitosan, or other *Demodex*-specific biomarkers that could be detected and quantified to correlate with mite numbers.

*Demodex* DNA can be quantified, for example, as the density of DNA copies coding for a particular *Demodex* target sequence (e.g., 18S rRNA as one non-limiting example). In some embodiments, a density (defined as the number of DNA copies coding for a target region of *Demodex* per ng of human gDNA ($\times 10^{-6}$) of *Demodex* can be a threshold to initiate therapy if greater than about 1, 2, 3, 4, 5, 6, 7, 8, 9, 10, 11, 12, 13, 14, 15, 16, 17, 18, 19, 20, or more.

An infestation could be further categorized as to causative species of *Demodex* (e.g., *Demodex folliculorum* vs *Demodex brevis*). *Demodex brevis* resides mostly within the meibomian and sebaceous glands. Treatment could be modified, enhanced, or targeted based on the dominant species, e.g., increasing delivery of the therapeutic formulation to selected glands, for example.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "applying an isoxazoline parasiticide to an eye" includes "instructing the applying an isoxazoline parasiticide to an eye." The ranges disclosed herein also encompass any and all overlap, sub-ranges, and combinations thereof. Language such as "up to," "at least," "greater than," "less than," "between," and the like includes the number recited. Numbers preceded by a term such as "approximately," "about,"

and "substantially," as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

What is claimed is:

1. A method for treating an ocular *Demodex* infestation in a human patient in need of treatment thereof, comprising:
topically administering directly to an ocular surface of one or more eyes of the human patient an ophthalmic composition;
wherein the ophthalmic composition comprises:
an effective amount of lotilaner, wherein the lotilaner is present at between about 0.10% and about 0.50% by weight with respect to the total weight of the composition;
a hydrogenated castor oil; and
a polysaccharide thickener.

2. The method of claim 1, wherein the ophthalmic composition is in eye drop form.

3. The method of claim 1, wherein the combination of the hydrogenated castor oil and the polysaccharide thickener forms a long-lasting film layer.

4. The method of claim 1, wherein the ophthalmic composition is characterized by a viscosity, wherein the viscosity is sufficiently high to cause the ophthalmic composition to spread over meibomian gland orifices on upper and/or lower lid margins upon blinking or closing of the eye and to slow evacuation of the ophthalmic composition through the puncta of the eye for at least 20 seconds.

5. The method of claim 1, wherein the lotilaner is present at about 0.25% by weight with respect to the total weight of the composition.

6. The method of claim 1, wherein the hydrogenated castor oil is present at about 5% by weight with respect to the total weight of the composition.

7. The method of claim 1, wherein the polysaccharide thickener comprises hydroxypropyl methylcellulose or carboxymethyl cellulose.

8. The method of claim 1, wherein the polysaccharide thickener is present at between about 0.1% and about 0.5% by weight with respect to the total weight of the composition.

9. The method of claim 8, wherein the polysaccharide thickener is present at about 0.2% by weight with respect to the total weight of the composition.

10. The method of claim 1, wherein the ophthalmic composition further comprises a preservative agent, wherein the preservative agent does not comprises lauralkonium chloride or benzalkonium chloride.

11. The method of claim 1, wherein the ophthalmic composition further comprises a preservative agent, wherein the preservative agent comprises lauralkonium chloride or benzalkonium chloride.

12. The method of claim 1, wherein the ophthalmic composition further comprises a preservative agent, wherein the preservative agent is present at between about 0.15% and about 0.4% by weight with respect to the total weight of the composition.

13. The method of claim 1, wherein the ophthalmic composition does not comprise tea tree oil.

14. The method of claim 1, wherein the ophthalmic composition is only locally therapeutically effective.

15. A method for reducing cylindrical eyelash dandruff in a human patient in need of treatment thereof, comprising:
topically administering directly to an ocular surface of one or more eyes of the human patient an ophthalmic composition;
wherein the ophthalmic composition comprises lotilaner,
wherein the ophthalmic composition is in eye drop form, and
wherein the ophthalmic composition is only locally therapeutically effective.

16. A method for reducing cylindrical eyelash dandruff in a human patient in need of treatment thereof, comprising:
topically administering directly to an ocular surface of one or more eyes of the human patient an ophthalmic composition;
wherein the ophthalmic composition comprises lotilaner,
wherein the ophthalmic composition is formulated as a gel, an ointment, or a cream, and
wherein the ophthalmic composition is only locally therapeutically effective.

* * * * *